United States Patent
Cordaro

(10) Patent No.: US 8,236,055 B2
(45) Date of Patent: Aug. 7, 2012

(54) INTERVERTEBRAL PROSTHESIS FOR SUPPORTING ADJACENT VERTEBRAL BODIES ENABLING THE CREATION OF SOFT FUSION AND METHOD

(75) Inventor: Nicholas M. Cordaro, Vista, CA (US)

(73) Assignee: Seaspine, Inc., Vista, CA (US)

( * ) Notice: Subject to any disclaimer, the term of this patent is extended or adjusted under 35 U.S.C. 154(b) by 1003 days.

(21) Appl. No.: 12/086,513

(22) PCT Filed: Dec. 14, 2006

(86) PCT No.: PCT/US2006/047902
§ 371 (c)(1), (2), (4) Date: Jun. 13, 2008

(87) PCT Pub. No.: WO2007/075411
PCT Pub. Date: Jul. 5, 2007

(65) Prior Publication Data
US 2009/0118836 A1    May 7, 2009

Related U.S. Application Data

(60) Provisional application No. 60/751,182, filed on Dec. 16, 2005, provisional application No. 60/797,731, filed on May 4, 2006, provisional application No. 60/834,587, filed on Aug. 1, 2006.

(51) Int. Cl.
*A61F 2/44*     (2006.01)
(52) U.S. Cl. .................................... 623/17.11
(58) Field of Classification Search ..... 623/17.11–17.16
See application file for complete search history.

(56) References Cited

U.S. PATENT DOCUMENTS

| | | | |
|---|---|---|---|
| 3,951,366 A | 4/1976 | Abernathy et al. |
| 4,309,777 A | 1/1982 | Patil |
| 5,320,644 A | 6/1994 | Baumgartner |
| 5,344,459 A | 9/1994 | Swartz |
| 5,423,817 A | 6/1995 | Lin |
| 5,458,638 A | 10/1995 | Kuslich et al. |
| 5,522,899 A | 6/1996 | Michelson |
| 5,676,701 A | 10/1997 | Yuan et al. |
| 5,676,702 A | 10/1997 | Ratron |

(Continued)

FOREIGN PATENT DOCUMENTS

EP    0 346 269    12/1989
(Continued)

OTHER PUBLICATIONS

International Search Report and Written Opinion from PCT/US2009/039550 (a related application), dated May 29, 2009, 7 pages.

*Primary Examiner* — Eduardo C Robert
*Assistant Examiner* — Summer Kostelnik

(57) ABSTRACT

An intervertebral prosthetic disc for replacing a damaged natural disc includes upper and lower vertebral body engaging surfaces, an exterior wall and one or more generally vertically oriented bone channels of limited cross-sectional area to allow bone to form and fuse into continuous or discontinuous struts between the bodies. The stiffness of the disc, while supporting the bodies, allows the distance therebetween to narrow sufficiently when subjected to a predetermined load such as the patient standing, walking, etc., to transfer sufficient energy to the bone struts to create one or more nonunion joints or pseudoarthrosis at locations along the struts. The disc includes stops to limit the movement thereof to an amount sustainable by the disc without resulting in fatigue failure.

16 Claims, 28 Drawing Sheets

U.S. PATENT DOCUMENTS

| | | | |
|---|---|---|---|
| 5,749,916 A | 5/1998 | Richelsoph | |
| 5,861,041 A | 1/1999 | Tienboon | |
| 5,910,315 A | 6/1999 | Stevenson et al. | |
| 5,984,967 A | 11/1999 | Zdeblick et al. | |
| D425,989 S | 5/2000 | Michelson | |
| 6,113,637 A | 9/2000 | Gill et al. | |
| 6,129,763 A | 10/2000 | Chauvin et al. | |
| 6,136,031 A | 10/2000 | Middleton | |
| 6,143,031 A | 11/2000 | Knothe et al. | |
| 6,162,252 A | 12/2000 | Kuras et al. | |
| 6,296,664 B1 | 10/2001 | Middleton | |
| 6,315,797 B1 | 11/2001 | Middleton | |
| 6,395,035 B2 | 5/2002 | Bresina et al. | |
| 6,447,547 B1 | 9/2002 | Michelson | |
| 6,656,224 B2 | 12/2003 | Middleton | |
| 6,696,073 B2 | 2/2004 | Boyce et al. | |
| 6,736,850 B2 | 5/2004 | Davis | |
| 6,749,635 B1 | 6/2004 | Bryan | |
| 6,749,636 B2 | 6/2004 | Michelson | |
| 6,989,032 B2 | 1/2006 | Errico et al. | |
| 7,318,840 B2 | 1/2008 | McKay | |
| 7,481,812 B2 | 1/2009 | Frey et al. | |
| 7,578,847 B2 | 8/2009 | Albert et al. | |
| 7,618,456 B2 | 11/2009 | Mathieu et al. | |
| 7,763,079 B2 | 7/2010 | McKay | |
| 2003/0199982 A1 | 10/2003 | Bryan | |
| 2005/0015150 A1 | 1/2005 | Lee | |
| 2006/0089719 A1 | 4/2006 | Trieu | |
| 2006/0200239 A1 | 9/2006 | Rothman et al. | |
| 2006/0200240 A1 | 9/2006 | Rothman et al. | |
| 2006/0200241 A1 | 9/2006 | Rothman et al. | |
| 2006/0200242 A1 | 9/2006 | Rothman et al. | |
| 2006/0200243 A1 | 9/2006 | Rothman et al. | |
| 2006/0217809 A1 | 9/2006 | Albert et al. | |
| 2006/0235523 A1* | 10/2006 | Gil | 623/17.12 |
| 2007/0016299 A1 | 1/2007 | Eckman | |
| 2008/0046082 A1 | 2/2008 | Lee | |
| 2008/0161927 A1 | 7/2008 | Savage et al. | |
| 2009/0005872 A1 | 1/2009 | Moumene et al. | |
| 2009/0138088 A1 | 5/2009 | Scribner et al. | |
| 2009/0143859 A1 | 6/2009 | McClellan, III et al. | |
| 2010/0168858 A1 | 7/2010 | Hardenbrook et al. | |

FOREIGN PATENT DOCUMENTS

| | | |
|---|---|---|
| FR | 2124815 | 1/1972 |
| WO | 2006/119088 | 11/2006 |
| WO | 2007/075411 | 7/2007 |

* cited by examiner

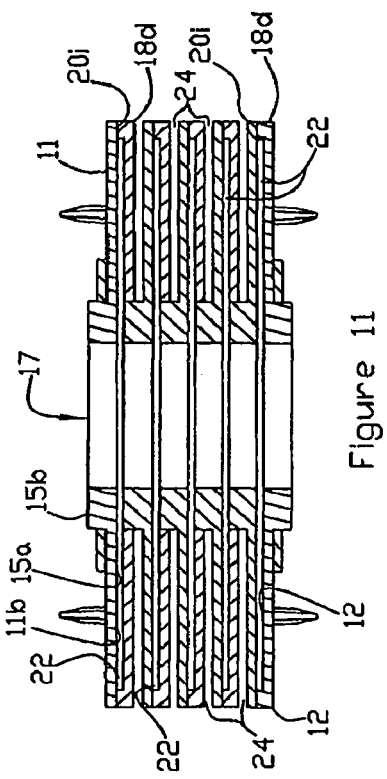
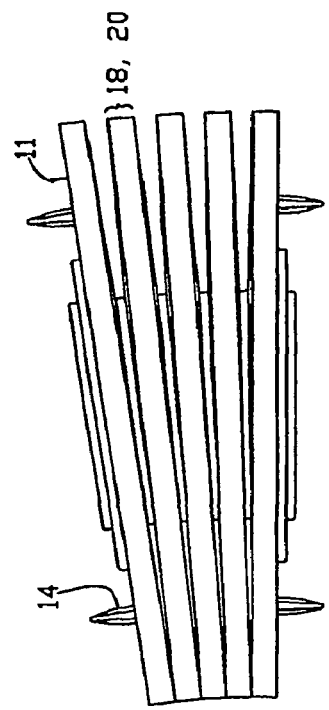
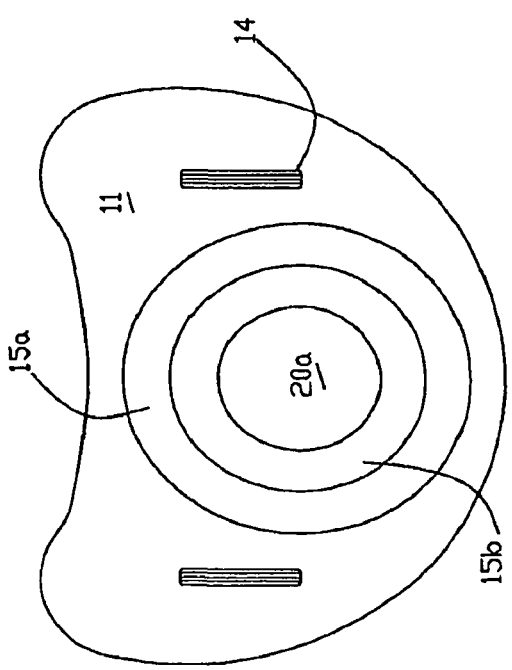
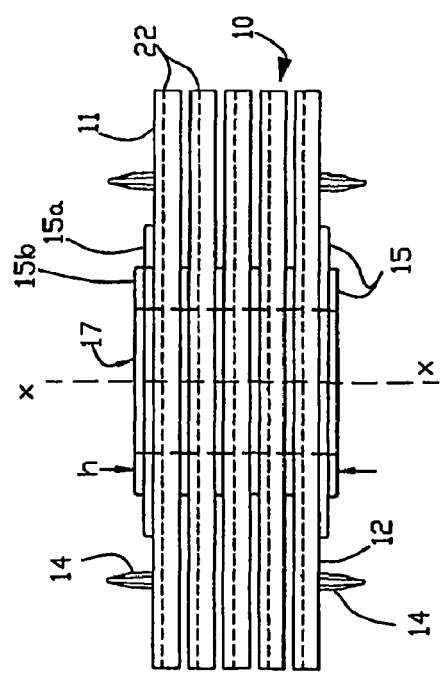

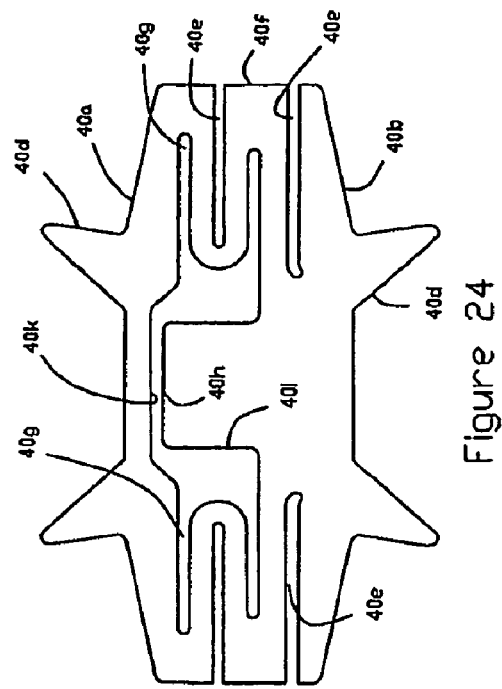
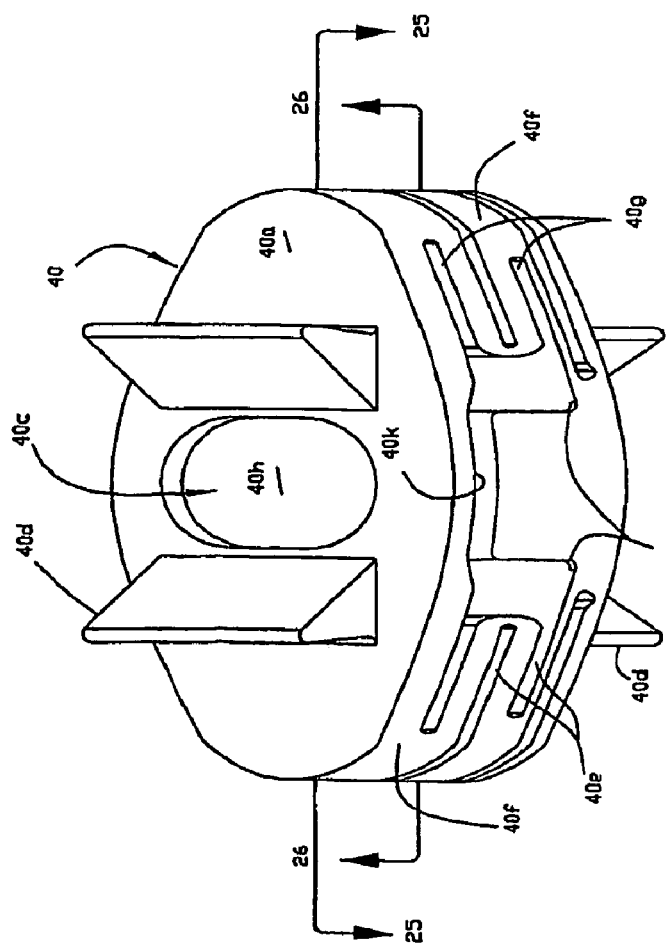

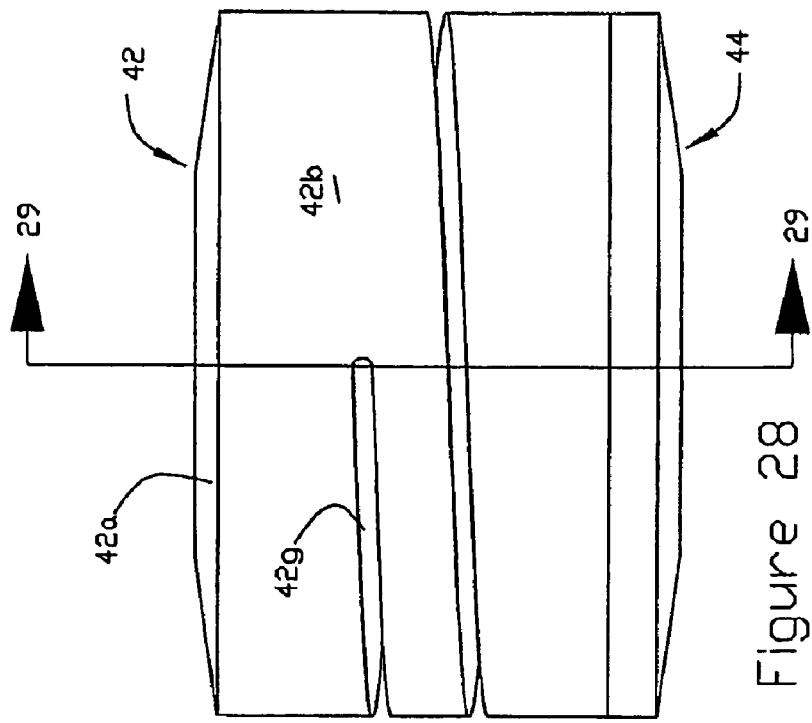
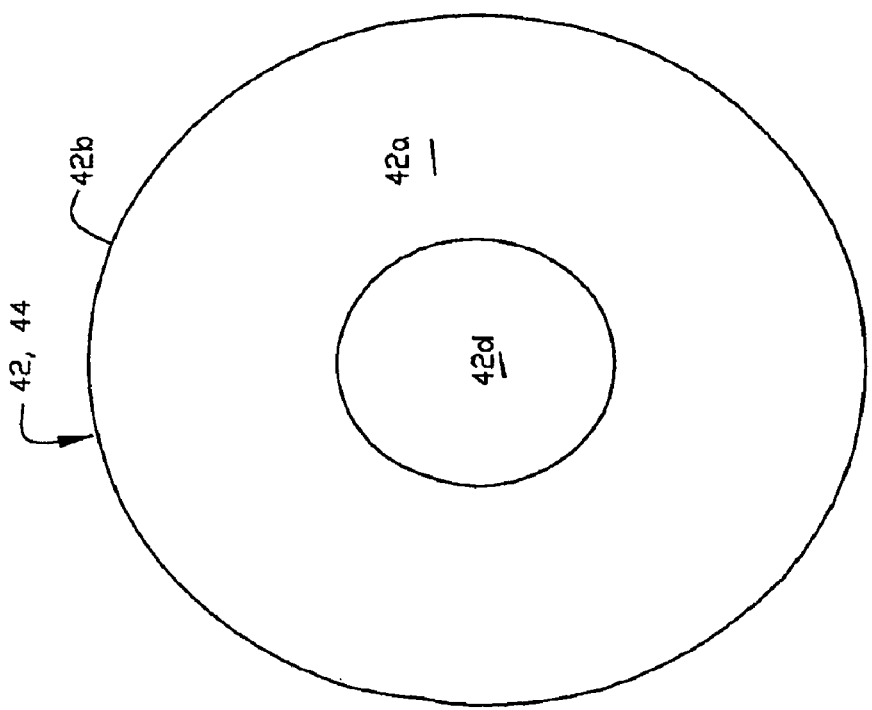
Figure 28
Figure 27

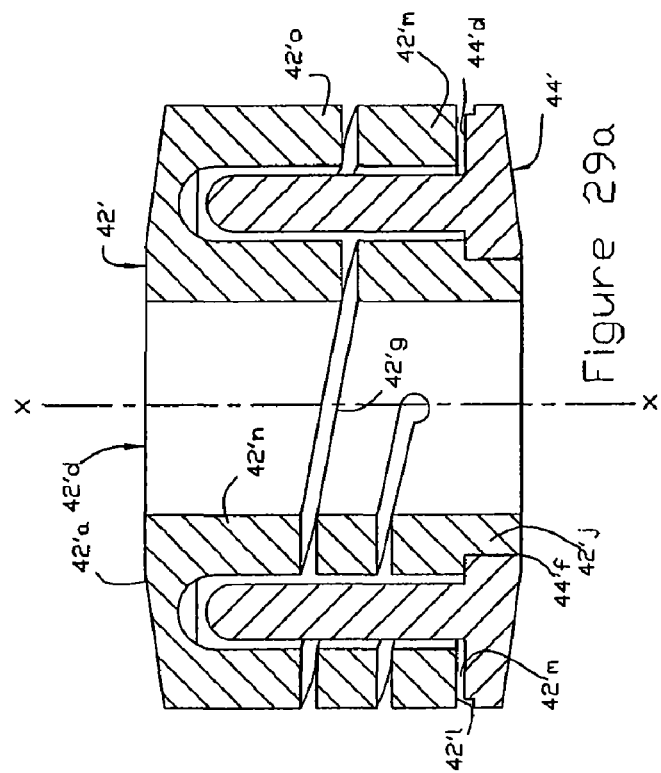
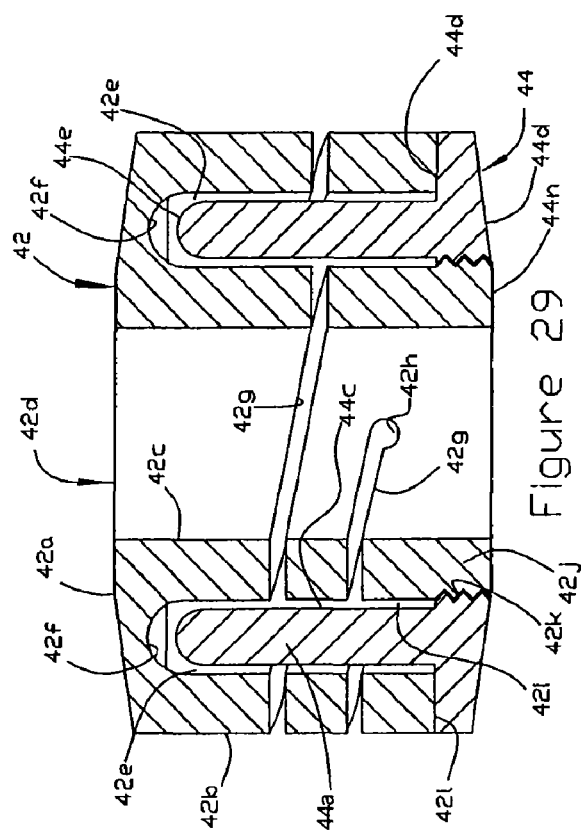

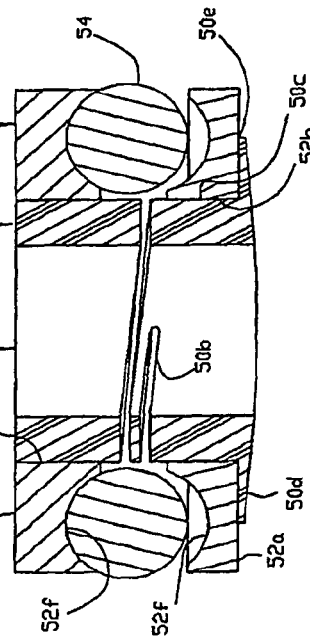
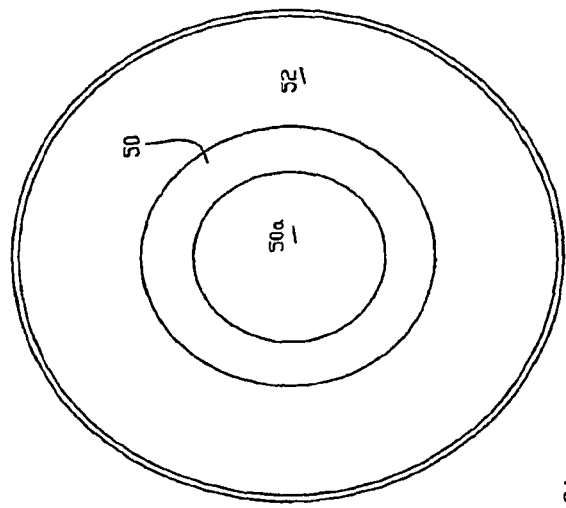
Figure 32
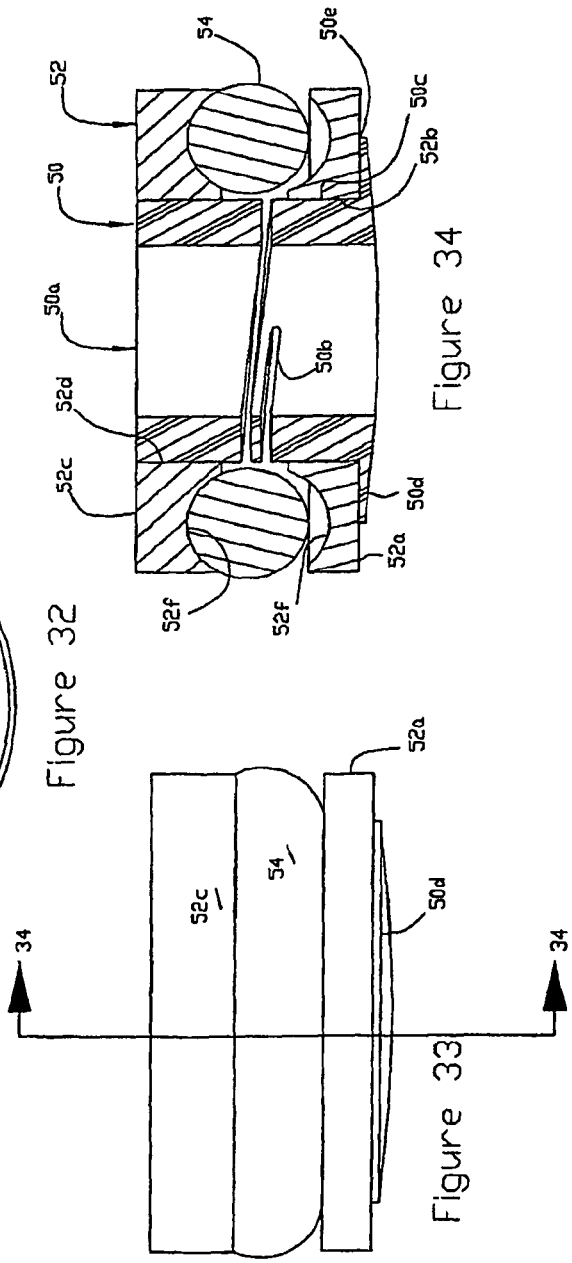
Figure 34
Figure 33

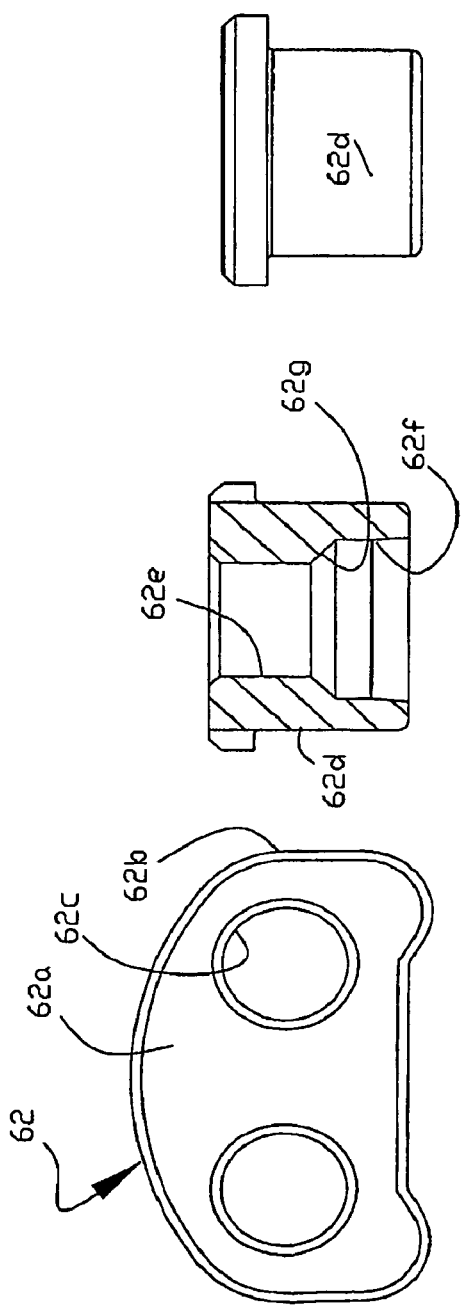
Figure 46
Figure 47
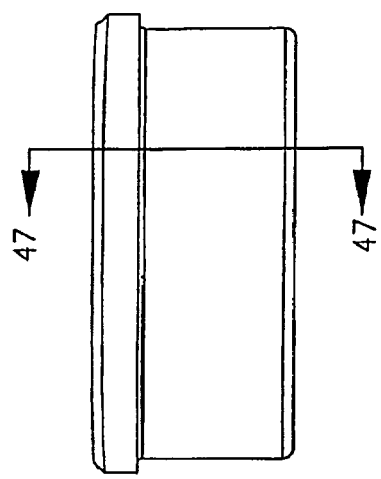
Figure 44
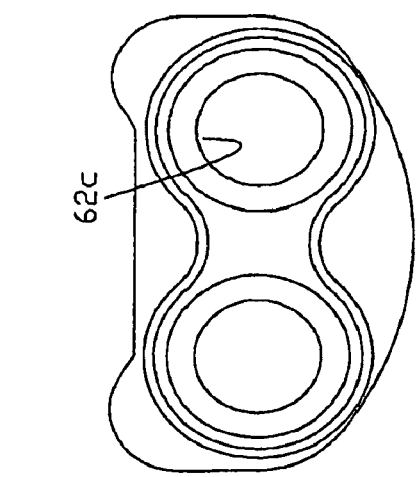
Figure 43
Figure 45

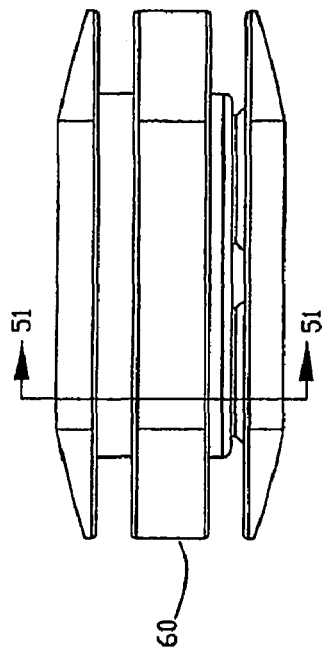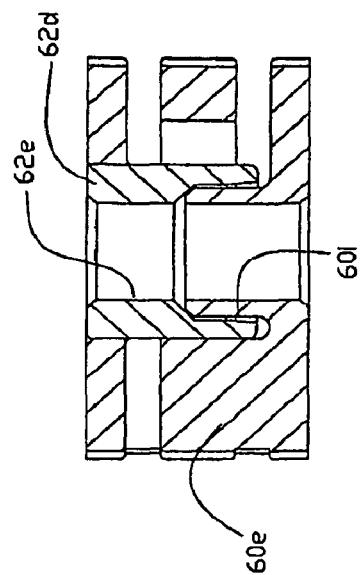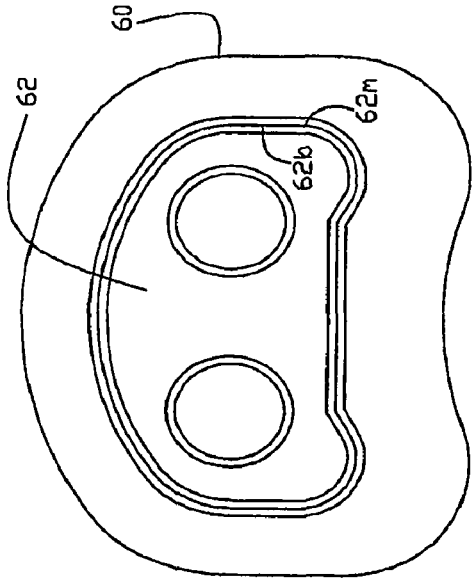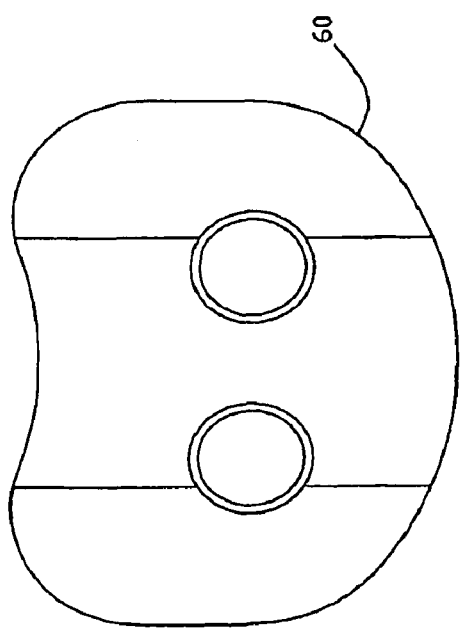

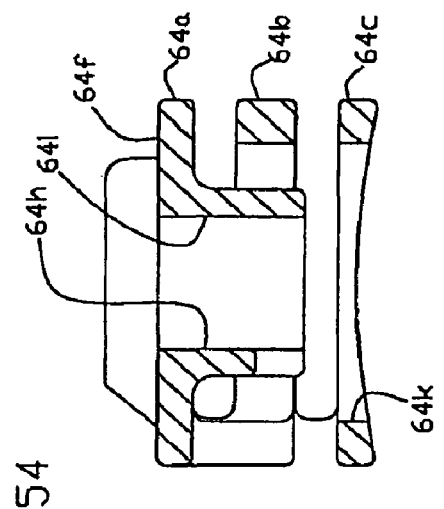
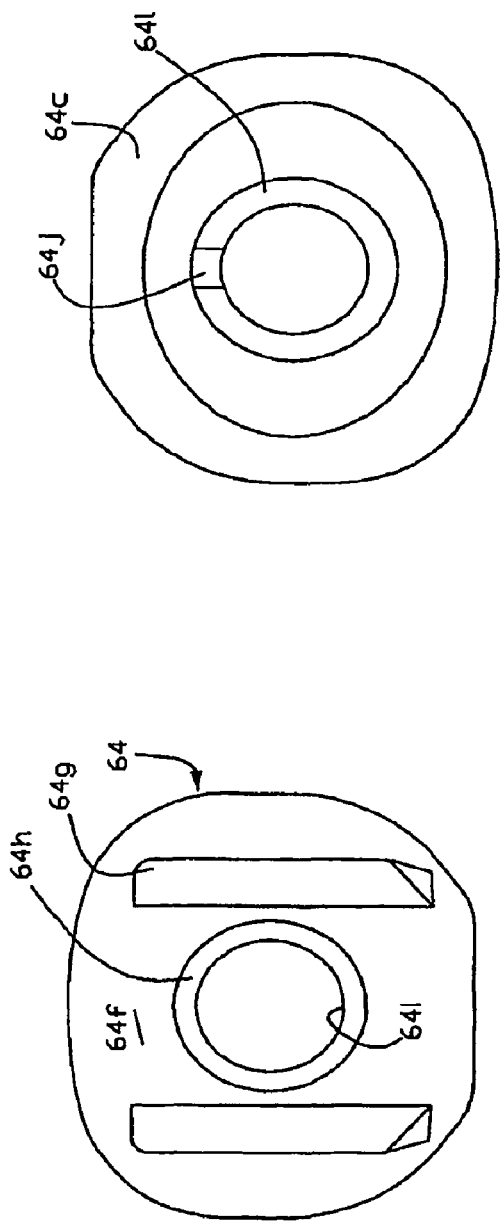
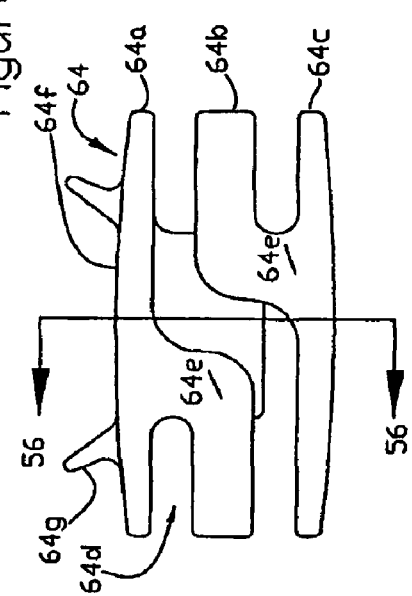
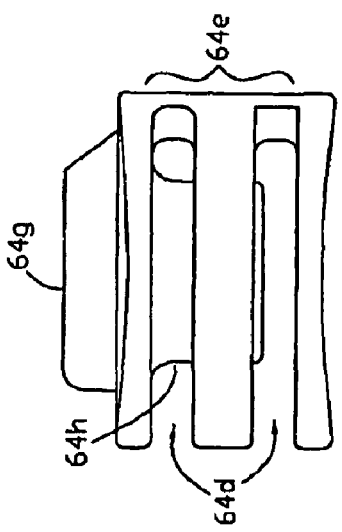
Figure 56
Figure 54
Figure 53
Figure 52
Figure 55

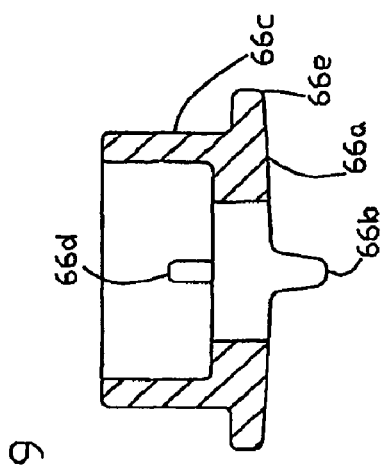
Figure 61
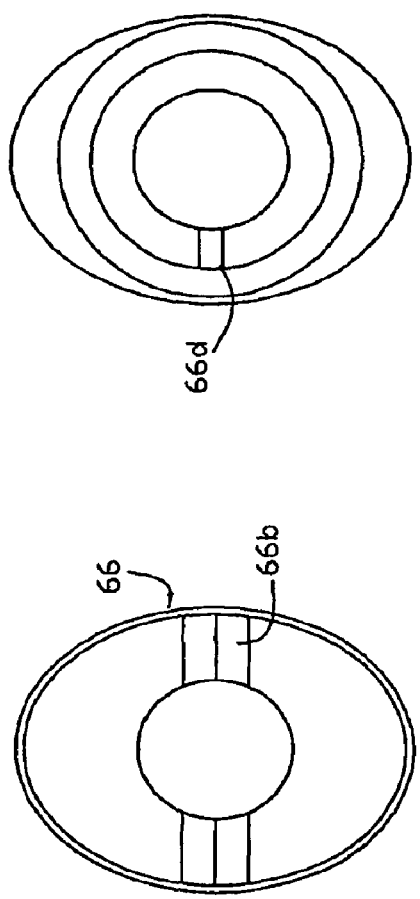
Figure 59
Figure 57
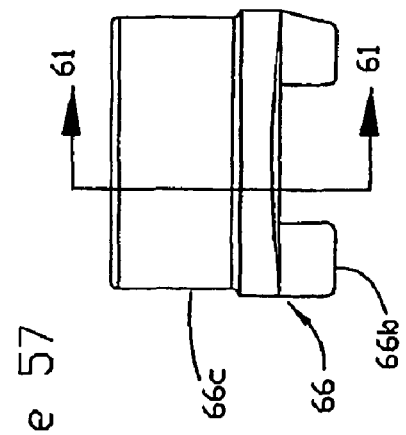
Figure 58
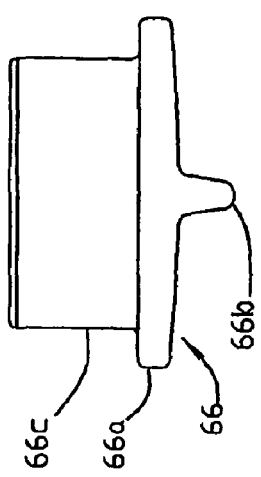
Figure 60

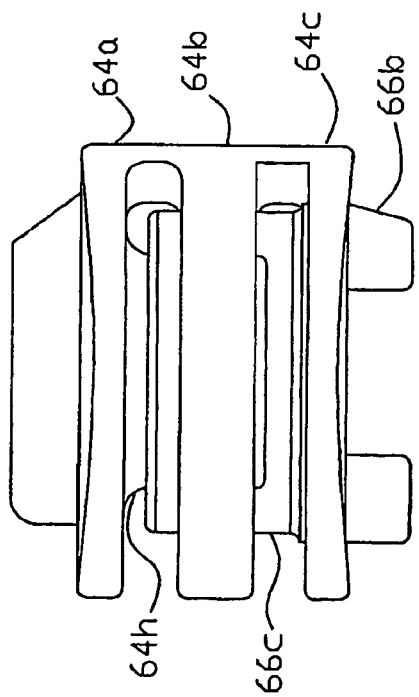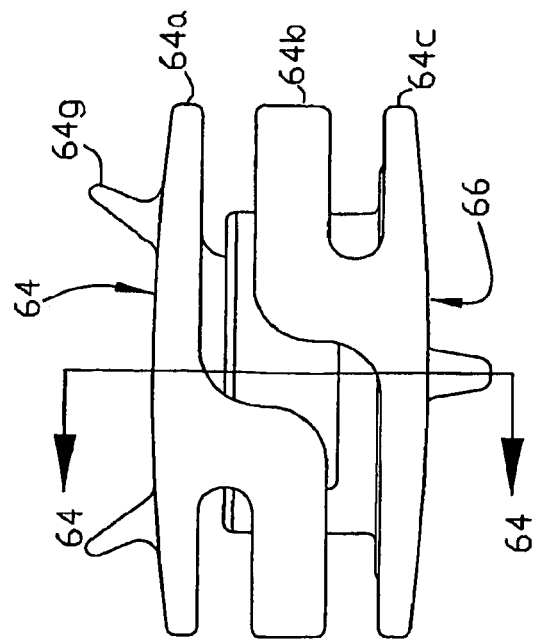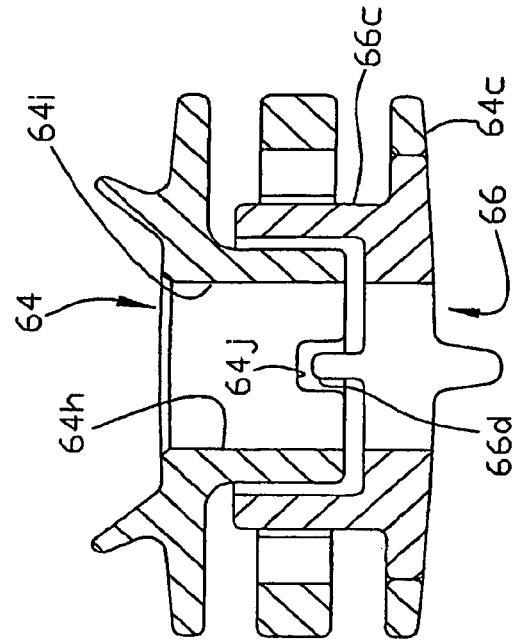

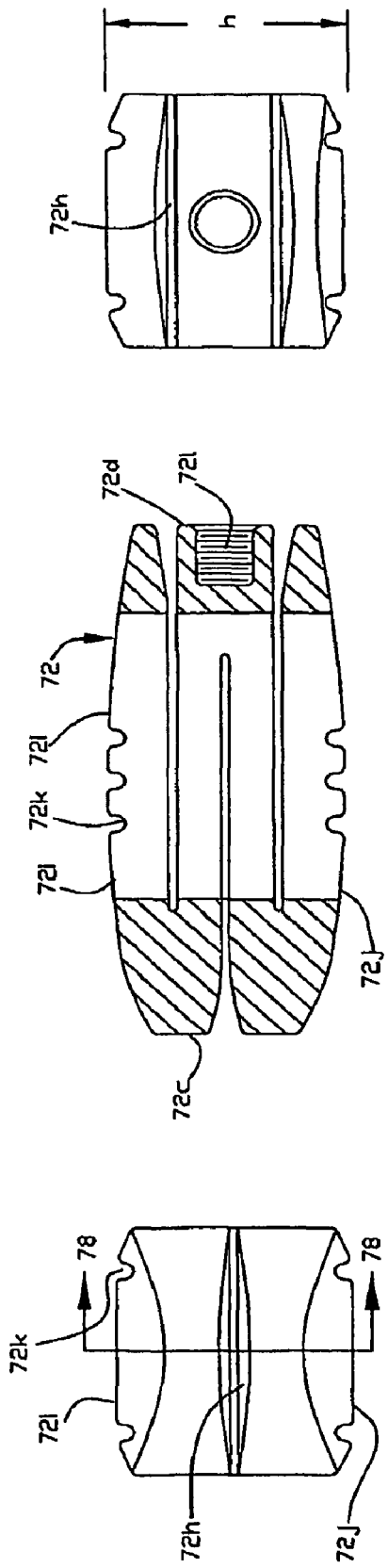
Figure 77
Figure 78
Figure 76
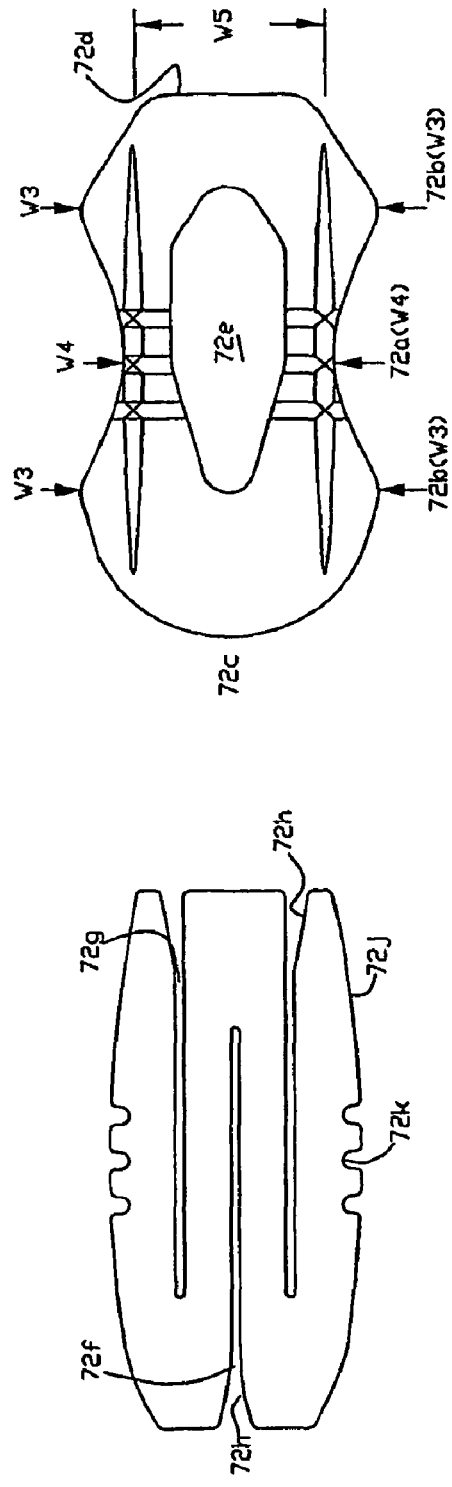
Figure 74
Figure 75

INTERVERTEBRAL PROSTHESIS FOR SUPPORTING ADJACENT VERTEBRAL BODIES ENABLING THE CREATION OF SOFT FUSION AND METHOD

RELATED APPLICATIONS

This application claims priority based on U.S. Provisional Application Ser. No. 60/751,182 for a Spinal Motion Restoring Device filed Dec. 16, 2005 ("'182 application"); Ser. No. 60/797,731 for a Method of Creating Soft Fusion Between Adjacent Vertebral Bodies and an Interbody Spacer for Accomplishing the Same filed May 4, 2006 ("'731 application"); and 60/834,587 for Intervertebral Hybrid Prosthetic Disc filed Aug. 1, 2006 ("'587 application") for all common subject matter. The contents of said provisional applications are incorporated herein by reference.

TECHNICAL FIELD

This application relates to a method and an interbody disc for restoring spinal motion between vertebral bodies between which the natural spinal disc has been removed in whole or in part.

BACKGROUND ART

In the field of spinal surgery, many treatment options exist to treat spinal pain, nerve impingement and spinal instability where a natural disc has failed in whole or in part. One such treatment is the removal of a damaged disc and its replacement with an intervertebral spacer which promotes fusion of bone between the separated vertebral bodies. This type of procedure when successfully completed, will result in a large bone mass between the vertebral bodies which will stabilize the column to a fixed position. See FIG. 1 where adjacent vertebral bodies 7 and 8 have been bridged with a solid mass of fused bone 9. This procedure is hereinafter referred to as rigid fusion. Also, see U.S. Pat. No. 6,447,547 to Michelson which discloses a spinal disc spacer intended to be infused with a solid, relatively motionless mass like FIG. 1. The success of a rigid fusion procedure appears to be one of many causes of adjacent segment disease. The lack of motion and the transfer of energy through the rigid fusion forces the adjacent structures to adjust to the higher loads and motions or fail. Adjacent segment disease occurs as they fail.

Ball and socket type disc arthroplasty devices have been tried for over 30 years. See U.S. Pat. Nos. 5,676,701 and 6,113,637. Their design rational is to allow motion in the hopes of reducing higher loads to adjacent structures. These have shown some success but also failures. A ball and socket type device requires no energy to rotate. Thus, the work absorbed by the device during rotation is zero. The rotation centers may be favorable at one specific instantaneous center of rotation present in a natural healthy disc, but is never correct nor favorable for all movements. This forces abnormal loads on adjacent structures. Materials needed for a stable ball and socket device are often very stiff or incompressible, thus any axial loads and especially shock loads through the device are almost completely transferred to the adjacent structures. A patient expecting a favorable outcome with a ball and socket lumbar disc arthroplasty device may find unfavorable results if repeated axial loads/shocks (along the spine axis) are a common occurrence.

U.S. Pat. No. 4,309,777 to Patil, discloses a artificial disc with internal springs intended to flex. The device relies solely on the internal springs to provide the mechanical flexing motion. U.S. Pat. No. 5,320,644 to Baumgartner, discloses a different type of a mechanical flexing device. This device uses overlapping parallel slits forming leaf springs, which may contact in abrupt load paths, yielding impact stress. U.S. Pat. Nos. 6,296,664, 6,315,797 and 6,656,224 to Middleton, attempt to solve the disadvantage of abrupt load paths with a device containing a pattern of slits to allow for a more continuous load path. Middleton's device further includes a large internal cavity defined by the exterior wall. The internal cavity may be packed with bone to rigidly fuse adjacent vertebral bodies or capped with opposing plugs which limit the device's motion. Middleton's devices are intended to have a continuous load path with no abrupt load stops. These devices must be sufficiently stiff to support the anatomical average and extreme loads, thus too stiff to provide soft fusion as defined hereinafter. U.S. Pat. No. 6,736,850, to Davis, discloses a pseudoathrosis device containing small (0.25 to 2 mm inner diameter), flexible, permeable material tubes as to allow fibrous ingrowth. This device is very soft and may collapse under normal loads and will likely not form bone within the small inner diameters.

See published application nos. US20060217809A1; US20060200243A1; US20060200242A1; US20060200241A1; US20060200240A1; and US20060200239A1. It is the apparent attempt of the intervertebral prosthetic discs disclosed in these latter publications, to restore full intervertebral motion. However, these devices, as a result of their design, would be soft and very flexible resulting in artificial discs capable of absorbing little energy when subjected to shock loads. Computer simulations and mechanical validations of discs obviously patterned after some of these designs showed that it takes minimal loads (e.g., less than about 5 lbs for the cervical and less than 20 lbs for the lumbar) to compress the devices. While the weight required to be supported by an individual's spinal column will, to a great extent, depend on the individual's size, the weight to be supported in the cervical, thoracic and lumbar regions, will range from about 5 to 30 lbs, 30 to 60 lbs and 60 to 150 lbs or more in the cervical, thoracic and lumbar regions, respectively. Computer simulations also demonstrated that the use of a spiral slot or slit extending from the outer to the inner wall and encircling the disc two or more times as is illustrated in some of the publications is probably the reason for this lack of stiffness. A device which is too soft, will fully collapse when the patient is vertical, allowing for no additional movement to absorb impact energy. These types of soft spring devices, believed to have a stiffness of about 2.0 newtons (N)/mm, for use in the cervical region, and about 22.0N/mm in the lumbar region. Some of the patents/publications do show a vertical hole in the device, but apparently it came about for manufacturing purposes not for functionality. These patents do not describe or imply an intended fusion.

Several of the above references disclose the use of mechanical springs or bellows as the means to separate adjacent vertebrae while providing movement therebetween during flexure and extension. Such spring arrangements, beside their other problems, such as fracture at attachment points to end plates, provide little shock and energy absorption capability because they either fully compress at normal loads, or fracture at high loads.

There is a need for an intervertebral disc replacement or spacer for simulating the motion and energy shock absorption characteristics of a natural disc. To this end my novel intervertebral disc and method relies on a combination of mechanical flexure elements and bone and/or soft tissue infiltration within the disc to accommodate such motion and energy absorption.

SUMMARY OF THE INVENTION

Overview

A desirable condition, which I term soft fusion, can be created between a patient's adjacent vertebral bodies in which the natural disc has failed in whole or in part by a) removing the failed disc or failed portion thereof; b) installing an artificial intervertebral disc between the two vertebral bodies; c) the disc providing one or more selected continuous or discontinuous channels of limited size for bone to form and fuse into one or more continuous or discontinuous struts between the vertebral bodies; d) the device being stiff enough to support the bodies in their natural spaced relationship while allowing limited motion and flexible enough to transfer sufficient energy to the bone struts to create one or more conditions of nonunion joints or pseudoarthrosis resulting in living nonrigid bone growth; and e) the disc being further arranged to limit its movement to an amount which is sustainable by the disc without resulting in fatigue failure during an anticipated lifetime.

The cortical/cancellous bone of a vertebrae, particularly in the lumbar region, is very stiff. For example, a vertebral body 30 mm in diameter with cortical bone around the outer 5 mm and cancellous bone (softer bone) on the inner area, which is 25 mm in height, will have an axial stiffness of approximately 235,000 N/mm or 235 KN/mm. The stiffness (axial) of a disc enabling soft fusion in accordance with the present invention should be between about 50 to 4000 N/mm, preferably within the range of about 200 to 1500 N/mm and most preferably between about 400-800N/mm. The size of the bone accommodating channel(s) should occupy about 10-35% (or less) and preferably about 12% to 25% of the total area of the disc facing the vertebral body to be supported.

A condition of soft fusion is illustrated in FIG. 2 where a centralized bone strut 6 of limited dimensions is allowed to form within an open core or bone channel 17 of an interbody disc or spacer 10 to be described in more detail in connection with FIGS. 3-10. The bone strut 6, extending between the vertebral bodies, has formed regions of pseudoarthosis or nonunion locations 6a. The nonrigid bone struts along with the mechanical properties of the artificial disc accommodate additional energy absorption with increased movement per given load simulating, to a significant extent, the performance of a natural disc.

Preferably in addition to the inclusion of an open continuous or discontinuous core(s) 17 to accommodate the bone strut(s) the spacer will include generally horizontally oriented tissue accommodating channels ("tissue channels") 22, 24 to promote vascularization and fibrous tissue ingrowth. FIG. 2a illustrates vascularization taking place within the tissue and bone channels. I refer to a disc which enables soft fusion as well as accommodates soft tissue infusion such as is demonstrated in FIG. 2 as a hybrid disc or device.

The added advantage of tissue channels in conjunction with the bone strut forming channel(s) is that upon each loading and unloading cycle of the spine, nutrients and cellular waste will be pumped through tissue channels forming fibrous tissue within the tissue channels (vascularization). The nutrients and cellular waste are also pumped in and out to the bone strut(s). The disc may be "tuned" to match the deflection per load ratios to that of a natural healthy disc. The additional benefit of the soft tissue vascular areas (or bone void areas) is that soft tissue provides little initial resistance to compression but provides increasing resistance to an increasing compressive load. The natural disc is also softer at lower compressions than at higher compressions (axial or bending). A soft fusion device, infiltrated with adequate soft tissue in the tissue channels or voids will produce a device which is nearly as soft as the implanted device or natural disc, when subjected to light loads, and then become stiffer with increased compression or bending, just as a natural disc will. This unique ability of a soft fusion device with applied vascular cellular inputs promotes a device which will closely mimic a natural healthy disc embracing the ability for the soft tissue to heal due to vasculization or to fuse upon a lack of device motion due to non use or device collapse or flexural element(s) failure.

A soft fusion device may take on many different forms and structures which will be as individualized as the anatomical location, desired outputs, and designer preferences but encompass the spirit of the invention. Obviously, the device must have a stiffness less than that of bone, but sufficient to maintain the supported vertebrae in a desired spaced relationship when the spine is subjected to light loads and flexible enough to transfer sufficient energy to bone strut(s) to create nonunion joints 6a when the spine is subjected to additional loading. Bone growth between the vertebral bodies outside of the selected bone accommodating channels is to be inhibited by limiting the available void volume, orientating the voids in a direction generally tangent to load paths, adding cellular inputs to specific void areas, filling the voids with a fluid or softer material and/or other means. The bone channels shown in this application are generally vertical and generally continuous. This is not a requirement for a soft fusion device. The device may have multiple channels in varying directions which do not need to be continuous. A discontinuous bone channel or an interrupted channel may extend ⅓ the total device height from one vertebral body and ⅓ the total distance from the opposing vertebral body and the device may be interrupted within the middle ⅓ of the device, for example. A channel extending at an angle from the endplate, at 60 degrees from vertical for example, may be useful to in allowing for more axial compression than a vertical channel. All these variations are allowable and in the spirit of a soft fusion device.

It may be possible for an artificial spinal prosthesis or disc to accomplish the same degree of limited motion, load dampening, and energy absorption of a soft fusion device but without the living bone struts (and preferably soft tissues layers) created by soft fusion, it will not have the unique ability to adapt to the patient's loading conditions, repair itself when broken, and have the unique ability to fully support the vertebral column in the unlikely event that the underlying interbody disc fails.

It is to be noted that the creation of a soft fusion state after the installation of a soft fusion hybrid device, in accordance with this invention, is dependent upon a patient's level of activity. For example, if a patient is sedimentary, i.e., moves very little, the bone formed with the channel(s) will become dense and rigid limiting the motion and energy absorption while protecting the spinal column stability. If the patient is more active, i.e., subjecting the struts and the device to additional loads, e.g., walking, lifting, etc., the bone core(s) will be less solid, i.e., fractured, not fully formed and/or infiltrated by soft tissue, allowing for more motion and energy absorption. This type of soft fusion/hybrid device will be able to change throughout the life of the patient, just as the body is able to remodel for given inputs. If the mechanical dampening and flexible members of a soft fusion device fatigue, crack and fail, the device will slightly collapse. The collapse will limit the motion and eliminate the dampening action of the device thus transferring the energy to the supporting bone strut(s), promoting additional bone fusion and support.

Mathematical Rational

The theory behind soft fusion may be best understood by analyzing only the differences between a soft and rigid fusion rather than attempting to analyze actually true loads, deflections, and energy absorption capabilities. This is done by starting with basic equations.

Axial Deflection ($\delta$) in the cephalic/caudal direction is equal to, $$\delta = \frac{PL}{AE}, \quad \text{(Eqn. 1)}$$

where P is the applied force, L is the length of the strut (disc height), A is the cross-sectional area and E is the modulus of elasticity.

Bending curvature $$\left(\frac{1}{\rho}\right)$$

either in flexion/extension or lateral bending is equal to:

$$\frac{1}{\rho} = \frac{M}{EI}, \quad \text{(Eqn. 2)}$$

where M is the applied bending moment and I is the moment of inertia.

Soft fusion works by displacing under applied forces more than possible with a ridged fusion. Strain energy (U) is defined as the energy uptake or energy absorbed by the deformation of the material by the applied load or:

$$U = \int_0^{x1} P * dx \quad \text{(Eqn. 3)},$$

where P in an applied force and the integral of x from 0 to x1 is the deformation. Deformations noted in equations 1 and 2 may be inserted into equation 3 to determine the actually strain energy.

Many assumptions must be made to analyze the forces and deflections through the vertebral column and associated structures in order to accurately determine strain energy or energy absorption. However, the validity of soft fusion may be proven by simply comparing the variables unique between soft and rigid fusions. For the abovementioned device these are 1) the cross-sectional area of the bone strut verse the cross-sectional area of a rigid fusion 2) the presence or absence of the device in conjunction with the bone strut and for sake of comparison to arthroplasty ball and socket devices, 3) the modulus of elasticity.

To first look at the axial energy absorbed with the first set of variables we only need to define the cross-sectional area of a soft fusion as approximately 0.785 cm^2 and the cross-sectional area of a rigid fusion as 15.4 cm^2. These are typical cross-sectional areas seen within the lumbar region. By then setting the strain energy of a soft fusion to $U_S$ and that of a rigid fusion to $U_R$ the relation between the two becomes:

$$\frac{U_s}{U_r} = \frac{\int_0^{\delta s} P * d\delta s}{\int_0^{\delta r1} P * d\delta r} \quad \text{(Eqn. 4)}$$

With equal assumptions to both soft and rigid fusions and with all variables except the cross-sectional areas equal, equation 4 becomes:

$$\frac{U_s}{U_r} = \frac{\frac{1}{As}}{\frac{1}{Ar}} = \frac{Ar}{As} = \frac{15.4 \text{ cm}^2}{.785 \text{ cm}^2} = 19.6 \quad \text{(Eqn. 5)}$$

In other words, a fully formed soft fusion bone channel will absorb 19.6 times more axial energy than a rigid fusion based solely on the area of available bone. The soft fusion device will reduce this number to some degree, depending on the stiffness of the actual device. Such constricted bone growth should not fully form in active patients or become fractured with high patient generated forces. When this occurs the presence of nonunions and fibrous tissue within the defined strut location(s) will only aid the soft fusion energy absorption capabilities by softening the hybrid bone, tissue, and implanted device creating a condition of a controlled pseudoarthrosis.

By neglecting the minimal effects of the Soft Fusion device and only comparing the bone strut to a cobalt chromium ball and socket device we see that the strain energy relationship in axial compression is approximately equal to:

$$\frac{U_{SoftFusion}}{U_{CoCr}} = \frac{\frac{1}{As * E_{bone}}}{\frac{1}{A_{disc} * E_{COCR}}} = \frac{A_{disc} * E_{COCR}}{As * E_{bone}} = \frac{15.4 \text{ cm}^2 * 220 \text{ GPa}}{.785 \text{ cm}^2 * 17 \text{ Gpa}} = 253 \quad \text{(Eqn. 6)}$$

As seen in equation 6, a cobalt chromium articulating device is extremely poor at absorbing axial impacts.

Similar bending calculations are currently omitted because of their redundancies to this application but would show similar results.

Suitable Intervertebral Disc Structure for Enabling Soft Fusion

A preferred intervertebral motion restoring disc for supporting adjacent vertebral bodies in their natural spaced relationship after a natural disc has been partially or wholly removed in accordance with the present invention has upper and lower surfaces for engaging the faces of the vertebral bodies to be supported and a support structure between the surfaces having a stiffness within the range previously discussed. The disc defines one or more generally vertically oriented continuous or discontinuous bone growth channels of limited cross-sectional area enabling bone struts to form therein extending at least partially and preferably completely between the bodies. The disc (with its stiffness characteristics) and the resulting bone strut or struts are arranged so that predetermined axial and/or bending loads thereon, e.g., normal loads, loads associated with standing or walking, will not fully compress the disc allowing a narrowing of the distance between the supported bodies during normal motion and create one or more pseudoarthrosis or fibrous nonunion locations along the length of the strut(s) to provide soft fusion thereby limiting a complete rigid strut formation. The disc further fully compresses at predetermined excessive forces in order to protect the flexural members of the device from overloading and failure. The unique combination of one or more pseudoarthrosis bone struts and the mechanical disc supporting structure results in the condition of soft fusion as previously discussed. Such controlled and limited fusion, i.e., soft fusion, provides limited motion, both translational and rotational and energy and shock absorption characteristics surpassing that of a rigid fusion while preserving vertical column stability.

First, vertebral column stability is particularly important in that it prevents disc induced or allowed kyphosis and scoliotic curvatures as seen with ball and socket type devices. Some prior art articulating devices will often settle into a fully rotated position when the soft tissue is unable to stabilize the spinal column. A soft fusion disc provides a force towards the central position assisting to stabilize the spinal column. Second, disc stability is important in that the continuous or discontinuous bone channels will likely form some degree of bone with soft tissue infiltration. This will greatly aid in preventing device expulsion, a failure mode seem with other non-fusion devices.

One such intervertebral disc acceptable for providing soft fusion and particularly designed for anterior insertion in the lumbar/thoracic region includes a pair of end plates (or layers) with each end plate having an outer intervertebral engaging surface for buttressing against a respective vertebral body and an inner surface. A plurality of interleaved first and second axial dampening plates (or layers) are sandwiched and secured between the inner surfaces of the end plates.

Each of the individual dampening plates define a peripheral outer wall and an inner generally cylindrical open bone accommodating core aligned along a longitudinal axis which will be generally aligned with the patient's spinal column when installed. Every other pair of axial dampening plates may be bonded, e.g., welded, together adjacent the inner core (or machined) leaving a generally planar space therebetween extending outwardly from the bonded area beyond the outer walls. The remaining pairs of axial dampening plates may be bonded, e.g., by welding, together along their peripheral walls (or machined) leaving a generally planar space therebetween extending from the bonded area to the open core. This arrangement provides alternating spaces extending from the core outwardly and from the peripheral walls inwardly which allows the end plates and the vertebral bodies to which they are secured to have limited translational motion parallel to the longitudinal or spinal axis and limited pivotal motion about the axis while dampening both motions. The channels formed between the plates and particularly the channels extending inwardly from the peripheral wall will accommodate tissue infusion and function as tissue channels.

Preferably the dampening plates are provided with one or more flexion slots between the outer peripheral walls and the inner cores to provide increased flexing action. The periphery of plates preferably follow the contour of the disc which they are to replace, e.g., an outer, generally convex, peripheral wall merging with a generally concave inner wall. As an option, a rotational dampening subassembly, to provide limited rotational motion between the end plates, can be inserted into the sandwiched axial dampening plates. Such assembly comprises an inner generally circular planar torsional dampening spring member with a helical slot, mounted between upper and lower torsional plates so that one of the torsional plates can rotate through a limited angle relative to the other. Alternatively, the spacer may be formed with about a 1½ turn or helical slot extending from the exterior wall to the central core(s) eliminating the interleaved plate construction as will become apparent in reference to the appended drawings.

The plates may be made of a suitable biocompatible material such as a titanium, cobalt or stainless steel alloy and or super elastic metals, e.g., nitinol, which in the sandwiched assembly, has sufficient strength and flexibility (stiffness) to withstand the anticipated stresses while providing the desired motion requirements to allow nonrigid bone struts to form within the open core.

In one method of construction the assembly is built plate by plate (or layer by layer) with the individual plates joined by diffusion, laser or electron beam welding or perhaps with a mechanical interference fit only.

The assembly may be constructed in various configurations adapted to site specific in vivo locations such as anterior, anterior lateral, lateral, lateral posterior or posterior spinal interbodies, interspinous dampening spacers, interconnecting pedicle screw dampening members or other posterior element stabilization devices.

An intervertebral disc particularly designed for the cervical region of the spine is formed with upper and lower surfaces for engaging the respective vertebrae faces to be supported and a generally elliptical partially obstructed open core for accommodating the formation of one or more bone struts. The spacer includes generally planar semicircular soft tissue integration channels extending inwardly from a peripheral wall to a location short of the open core. The tissue channels are interleaved with planar channels extending outwardly from the core to a location short of the peripheral wall.

The structure and function of an intervertebral disc for creating soft fusion and method for accomplishing this desired condition are explained in more detail in the accompanying description of the preferred embodiments taken in conjunction with the appended drawings wherein like components (or locations) are given the same reference numerals.

BRIEF DESCRIPTION OF THE DRAWINGS

FIGS. 9 and 10 are top plan and front views, respectively, of the disc;

FIG. 11 is a cross-sectional view of the disc of FIG. 1 taken along lines 11-11;

FIG. 12 is a front elevational view of the disc showing articulated/pivotal motion between the end plates about the longitudinal axis;

FIGS. 23 and 24 are perspective and side elevational views, respectively, of an alternative embodiment of a disc primarily designed for the cervical region;

FIGS. 27-29 are top plan, side elevational and cross-sectional views of other interbody discs for providing increased rotational mobility;

FIG. 29a is a cross-sectional view of the disc of FIGS. 27 and 28 as modified to eliminate the threaded connection and provide a gap between the exterior walls of the upper and lower sections;

FIGS. 32-34 are top plan, side elevational and cross-sectional views of another disc embodiment;

FIGS. 43-47 are top plan, side elevational, bottom, end and cross-sectional views of an upper component of the two piece disc;

FIGS. 48-51 are top plan, side elevational, bottom and cross-sectional views of the assembled two piece disc;

FIGS. 52-56 are top plan, side elevational, bottom end and cross-sectional views of an upper component of an alternative two-piece disc;

FIGS. 57-61 are bottom plan, side elevational, top, end, and cross-sectional views of a base or bottom component of the two-piece disc;

FIGS. 62-64 are side elevational, end and cross-sectional views of the assembled two piece disc;

FIGS. 74-78 are top plan, side elevational, front end, rear end and cross-sectional views of an alternative posterior disc.

DESCRIPTION OF THE PREFERRED EMBODIMENTS

Figure 3:
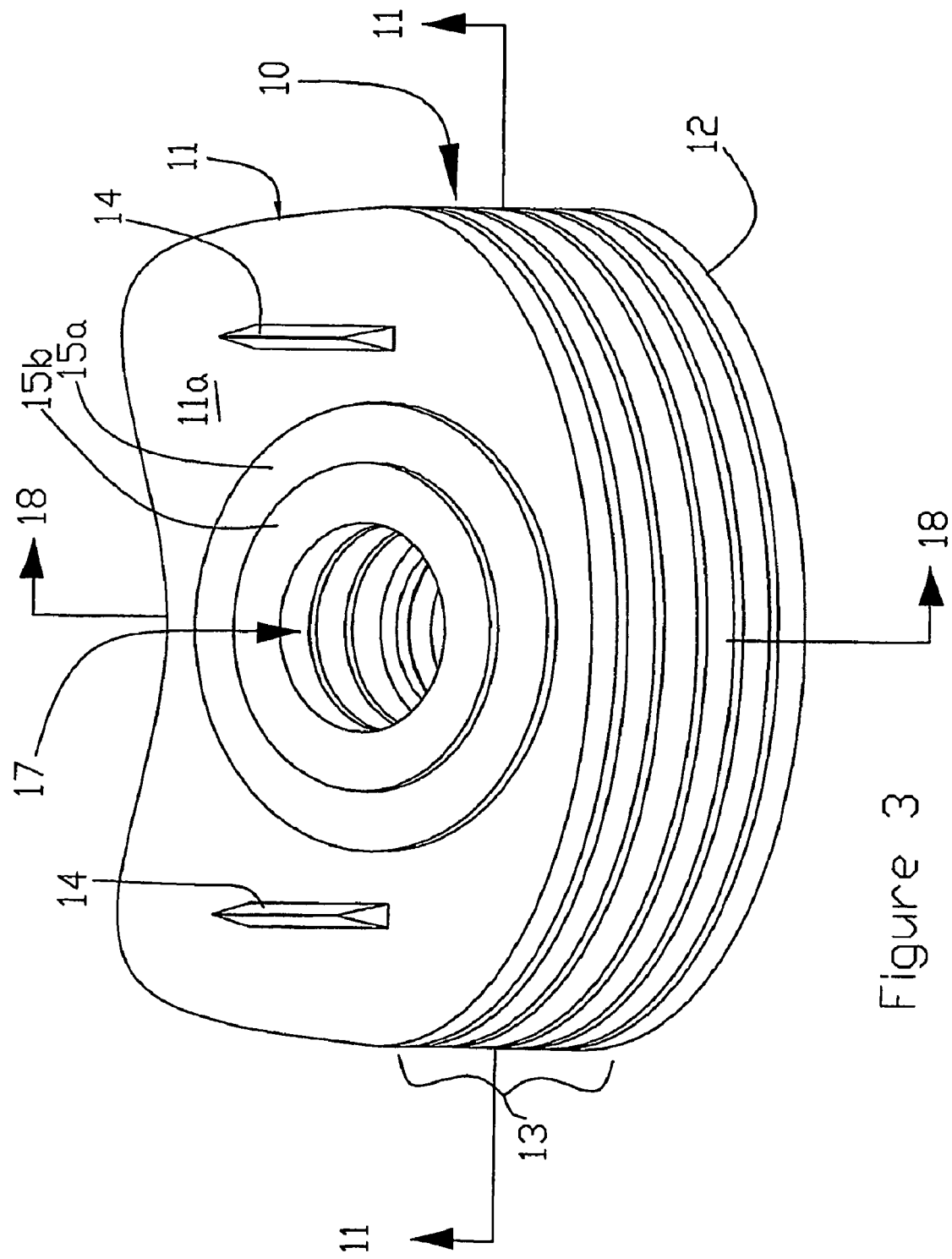
FIG. 3 is a perspective view of an anterior interbody disc in accordance with the present invention.

Referring now to FIG. 3 an upper end plate 11, providing an outer or cephalad surface 11a for buttressing against an upper vertebral body, is joined to a lower end plate 12, providing an outer or caudal surface 12a (not shown in FIG. 3). A group of interlocking interior plates or layers, collectively referred to as 13, are disposed between and joined to the inner surfaces 11b and 12b to form an anterior interbody device or artificial disc. See FIG. 11. The outer surfaces 11a and 12a of the end plates may be provided with an array of mechanical locking features such as the keels 14 or alternative geometric features and fixation rings 15a and 15b. The fixation rings may be constructed of an osteointegrative porous material which abut the edge of a hollow core or bone channel 17. As discussed previously, the core 17 accommodates bone growth to form a continuous or discontinuous strut (with nonunion locations) adjoining the separated vertebral bodies.

The fixation rings are stepped to provide additional purchase against the vertebral end plates and to fill the convex surface of the adjacent vertebral end plate. The core may be packed with bone to accelerate the formation of the strut or other material. The core 17 and the interior plates layers 14 may be, but preferably are not, shielded from surrounding tissues to prevent tissue integration or device particulate wear explosion. Dacron or polytetrafluroethylene are preferred material to provide device shielding if desired.

Figure 4:
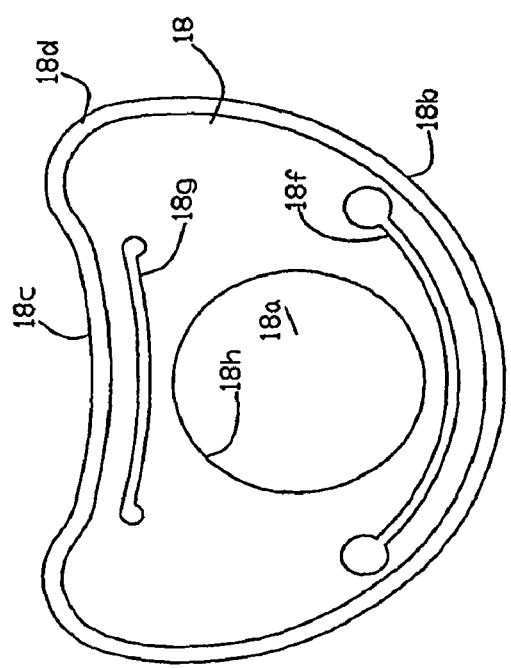
FIGS. 4 and 5 are plan and front views, respectively, of one of the outer or first dampening plates of the disc of FIG. 3.
Figure 5:
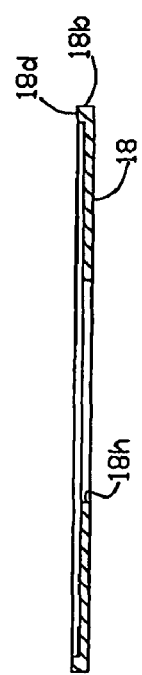

FIGS. 4 and 5 illustrate a first axial dampening plate 18 which forms one of the interior interleaved plates of the assembly or group 13. The plate 18 includes a central cylindrical opening 18a, a generally convex peripheral front wall 18b, merging with a generally concave back wall 18c, a protruding lip 18d, extending along the periphery, and optional front and back flexion slots 18f and 18g. The opening 18a is framed by a cylindrical wall 18h which is bonded to an inner shoulder of the second plate as will be explained.

Figure 6:
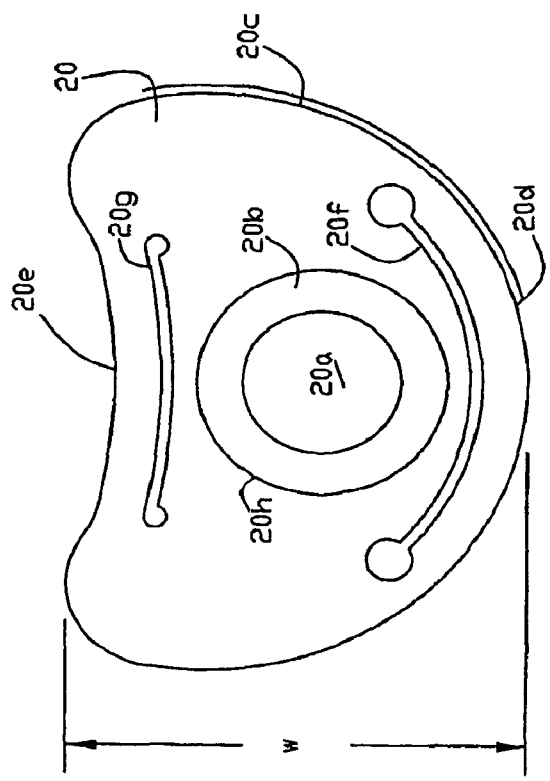
FIGS. 6 and 7 are plan and front views, respectively, of one of the inner or second dampening plates of the disc.
Figure 7:
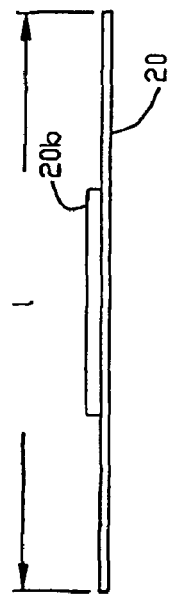

FIGS. 6 and 7 illustrate a second axial dampening plate 20. The second plates are interleaved with the first plates and disposed between and joined to the inner surfaces of the end plates 11 and 12 to form the motion restoring intervertebral device of the invention. The second plate 20 includes a central opening 20a, an upwardly protruding inner shoulder 20b surrounding the opening, a peripheral wall 20c in the form of front and back walls 20d and 20e, respectively. The second plates include flexion slots 20f and 20g which align with slots 18f and 18g in the assembled device.

Figure 8:
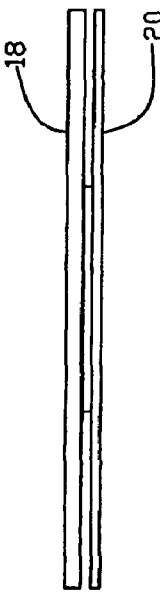
FIG. 8 is a front elevational view of the assembled plates of FIGS. 4-7.

FIG. 8 illustrates the first and second plates in an assembled condition with the first plate's inner surface 18h of the opening 18a being bonded to an outer surface 20h of the second plate's protruding lip 20b.

FIGS. 9 and 10 represent a top plan view and a front side view, respectively, of the assembled intervertebral device. It is to be noted that the second plates, when provided with an outer ring 15a, can be used as the end plates, as is shown in the cross-sectional view of FIG. 10. The horizontal dashed lines represent the bond or weld between the peripheral walls of the first and second plates although the welds would generally not be visible in the finished device. X-X represents the longitudinal axis of the device. The term axial loads, as used herein, refers to loads or forces directed along the X-X axis. The aligned openings 20a of the second plates represent the open core 17.

Figure 2:
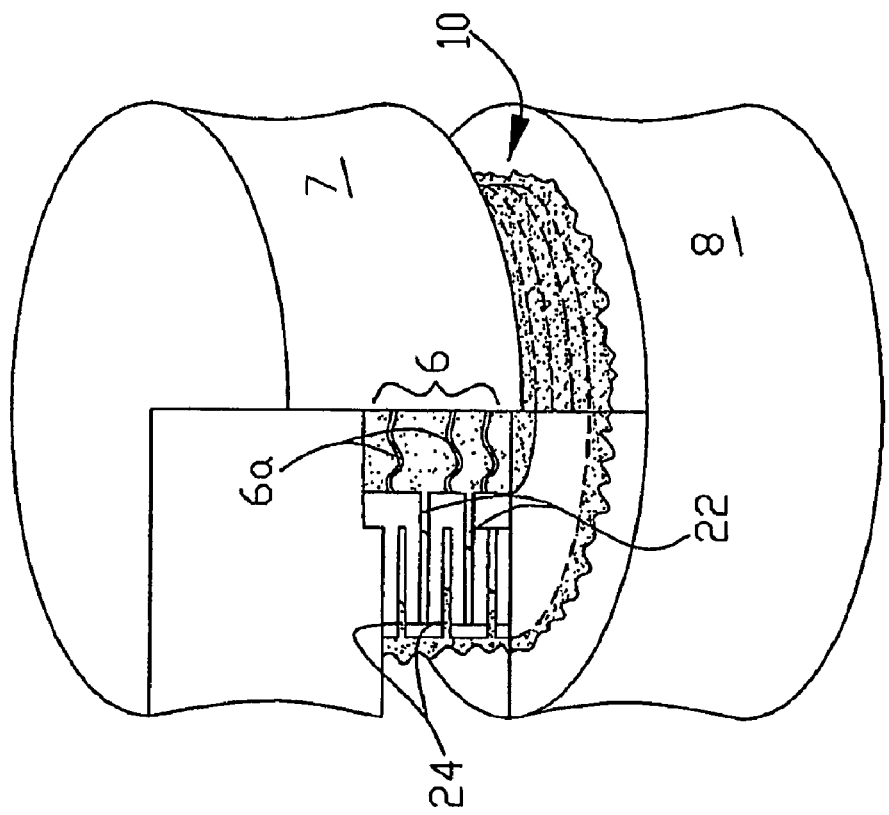
FIG. 2 is a perspective view, partially in cross-section, of adjacent vertebral bodies separated by an interbody disc and a central bone strut containing fibrous nonunion locations forming a soft fusion disc.
Figure 1:
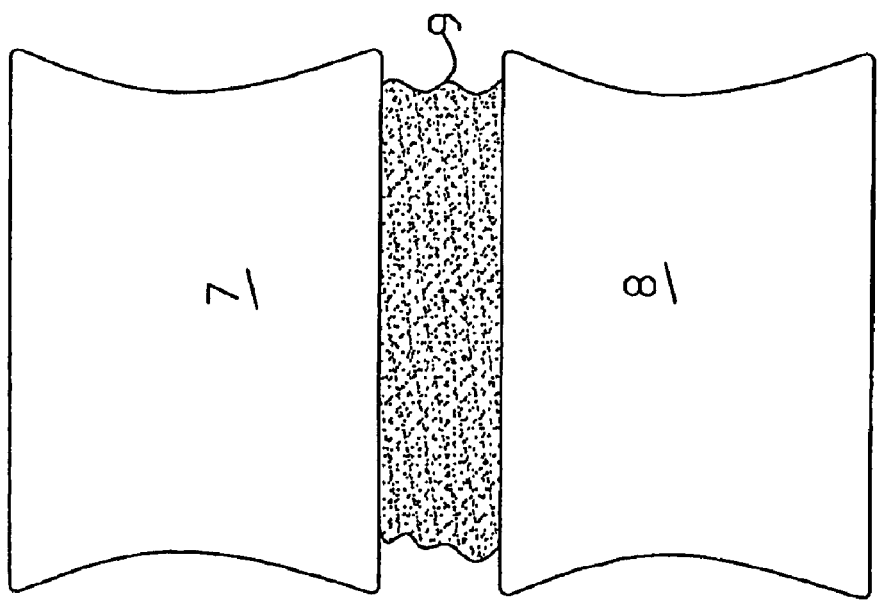
FIG. 1 is a side elevational view of adjacent vertebral bodies separated by a conventional rigid fused bone mass.
Figure 2A:
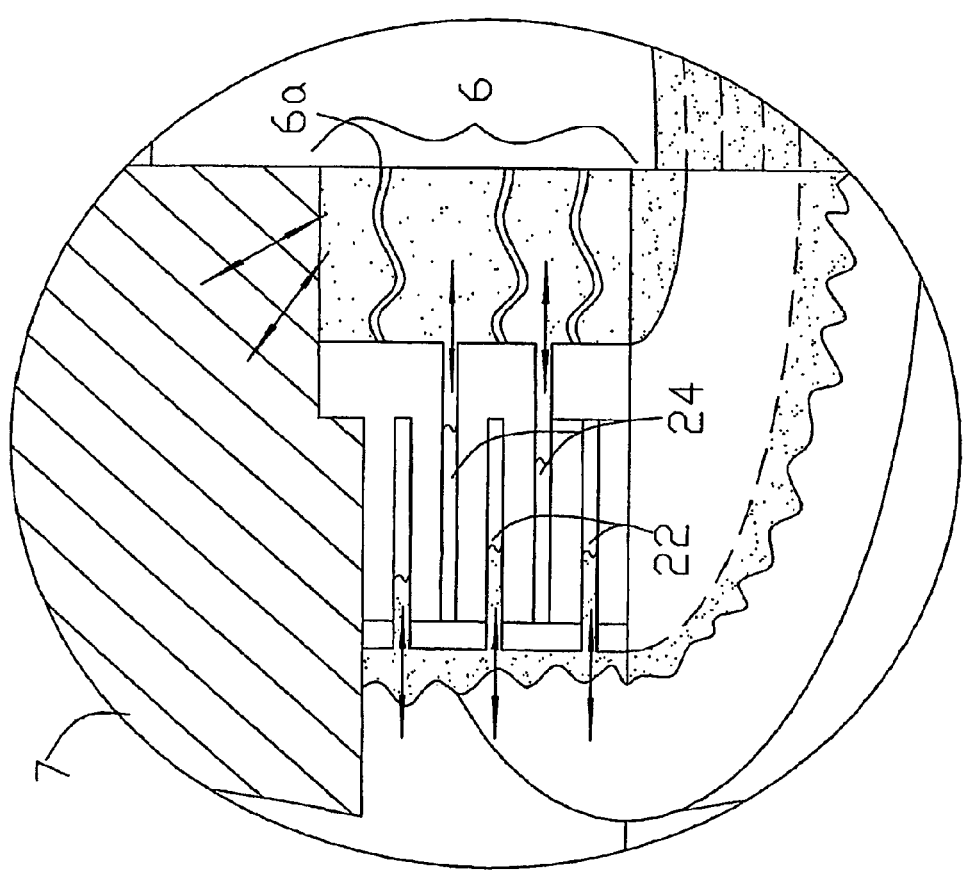
FIG. 2*a* is an enlarged partial view of the disc of FIG. 2 showing vascularization taking place within the tissue/bone channels.

Referring now to FIG. 11, a cross sectional view taken along line 11-11 of FIG. 1, the peripheral lip 18d of the first plates are bonded to a peripheral annular surface 20i on one side of the second plates leaving a generally planar space 22 extending inwardly from the bond or weld between 18d and 20i to the open core 17 as is shown in FIG. 9. The annular surface 18h, surrounding the opening 18a of the first plate, is bonded to the outer surface 20h of the next second plate to provide a generally planar space 24 extending outwardly from the bond (i.e., surface 20h) to the outside of the device as illustrated. This pattern is repeated with the plates being assembled one plate at a time until all plates are stacked and welded. If the device is diffusion welded, all plates may be stacked and welded at one time. The spaces 22 and 24 are preferably left open as shown and serve to allow the infusion of soft tissue as previously discussed.

The intervertebral disc, with its interleaved plates, has motion yet sufficient stiffness or strength to support the vertebral bodies (7, 8) in their natural spaced relationship while allowing limited motion and dampening the load applied to the bodies. When the separated vertebrae are subjected to normal loads, such as would be experienced by a person standing or walking, the plate will not be fully compressed allowing a narrowing of the distance between the vertebral bodies causing the bone strut formed in the core 17 to fracture or form fibrous nonunion joints at one or more locations along its length. Greater loads, such as jogging or lifting heavy objects, will further aid this process of promoting nonunions.

The fatigue life of the device is preserved by the internal spaces 22 and 24 as shown in FIG. 11 which spaces are preferably left open to accommodate soft tissue ingrowth therein forming a hybrid device. The individual plates or layers may flex, bend (and/or rotate with an optional torsional dampening subassembly to be described) as designed until they deflect to a point collapsing the internal spaces or preferably compressing tissue infused therein. Once the internal spaces are collapsed with or without tissue therein, the individual plate's movement will be stopped by an adjacent plate. All plates or layers are designed so that movement within these internal spaces will not fatigue the material, thus preserving the fatigue life of the device.

FIG. 12 is a front view illustrating an assembled intervertebral device under going articulation.

Figure 15:
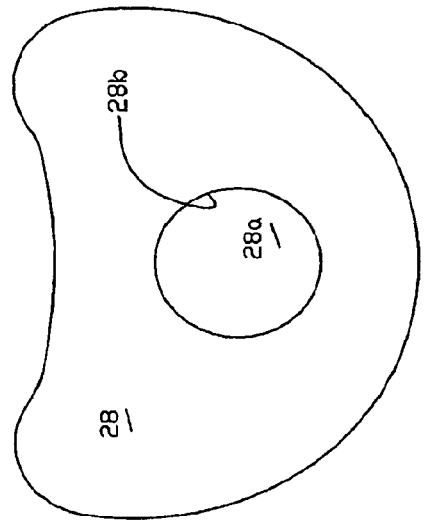
FIG. 15 is a plan view of an inner torsional dampening spring member of the subassembly.
Figure 13:
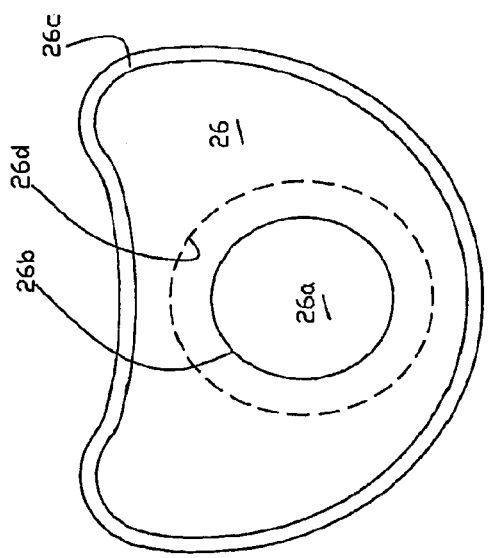
FIGS. 13 and 14 are top plan views, respectively, of the upper and lower torsional plates of a torsional dampening subassembly.
Figure 16:
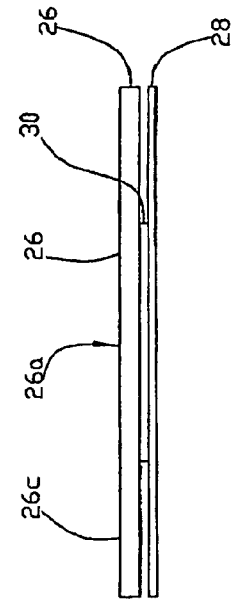
FIG. 16 is a front view of the assembled torsional dampening subassembly.
Figure 14:
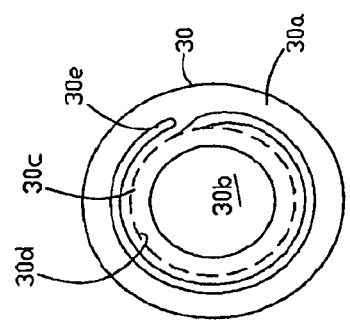

FIGS. 13 and 15 are top plan views of the outer plates 26 and 28 which together with a spring 30 (FIG. 14) form a torsional dampening subassembly shown in FIG. 16. Both plates follow the outside contour of the first and second plates and end plates. The upper plate 26 defines a central opening 26a (aligned along the longitudinal axis), a downwardly extending annular undercut 26b (shown in dashed lines), and an upwardly extending peripheral lip 26c (like the peripheral lip 18d). The lower plate 28 defines a central opening 28a surrounded by a surface 28b. A torsional spring member 30 includes peripheral area 30a, a central opening 30b, surrounded by an annular undercut 30c (shown in dashed lines) in FIG. 13 and with an undercut edge 30d, and a spiral slot 30e which allows limited rotation between the depending shoulder 30c and the peripheral area 30a.

Figure 17:
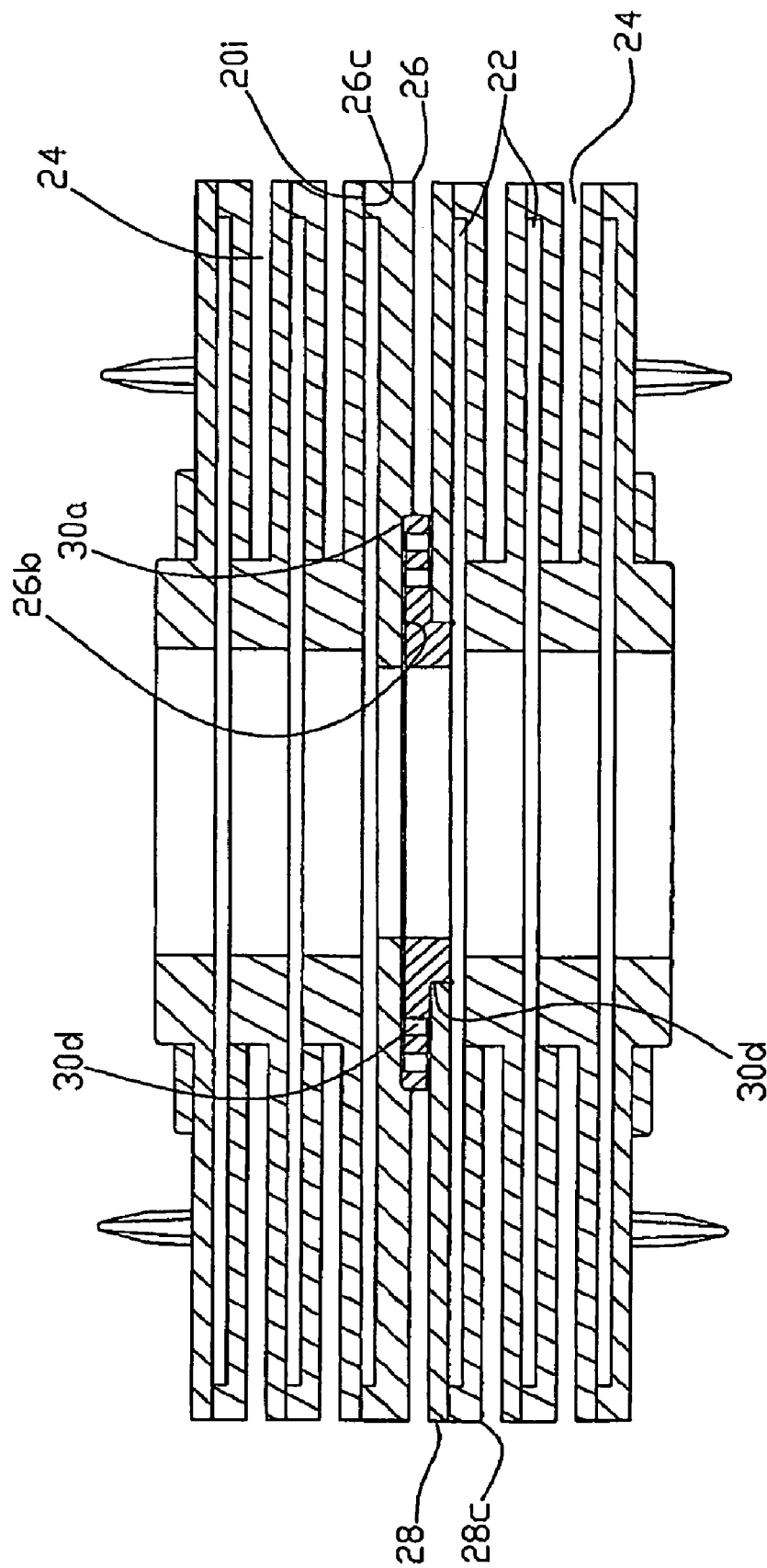
FIG. 17 is a cross-sectional view of the device of FIG. 3 incorporating the D rotational dampening subassembly, taken along lines 11-11 of FIG. 3.

FIG. 16 shows the torsional dampening subassembly in its assembled form while FIG. 17 illustrates a front cross-sectional view of the device of FIG. 1 including the addition of the torsional dampening subassembly. The lip 26c of the upper plate is bonded to the second plate's peripheral lower surface 20i. The edge 26d of the undercut 26b is bonded to the peripheral area 30a of the spring member 30 with the surface 30d of the spring member 30 being bonded to the surface 28b of the lower plate 28. The lower peripheral surface 28c of the lower plate 28 is bonded to the peripheral lip of the first plate as shown.

Figure 18:
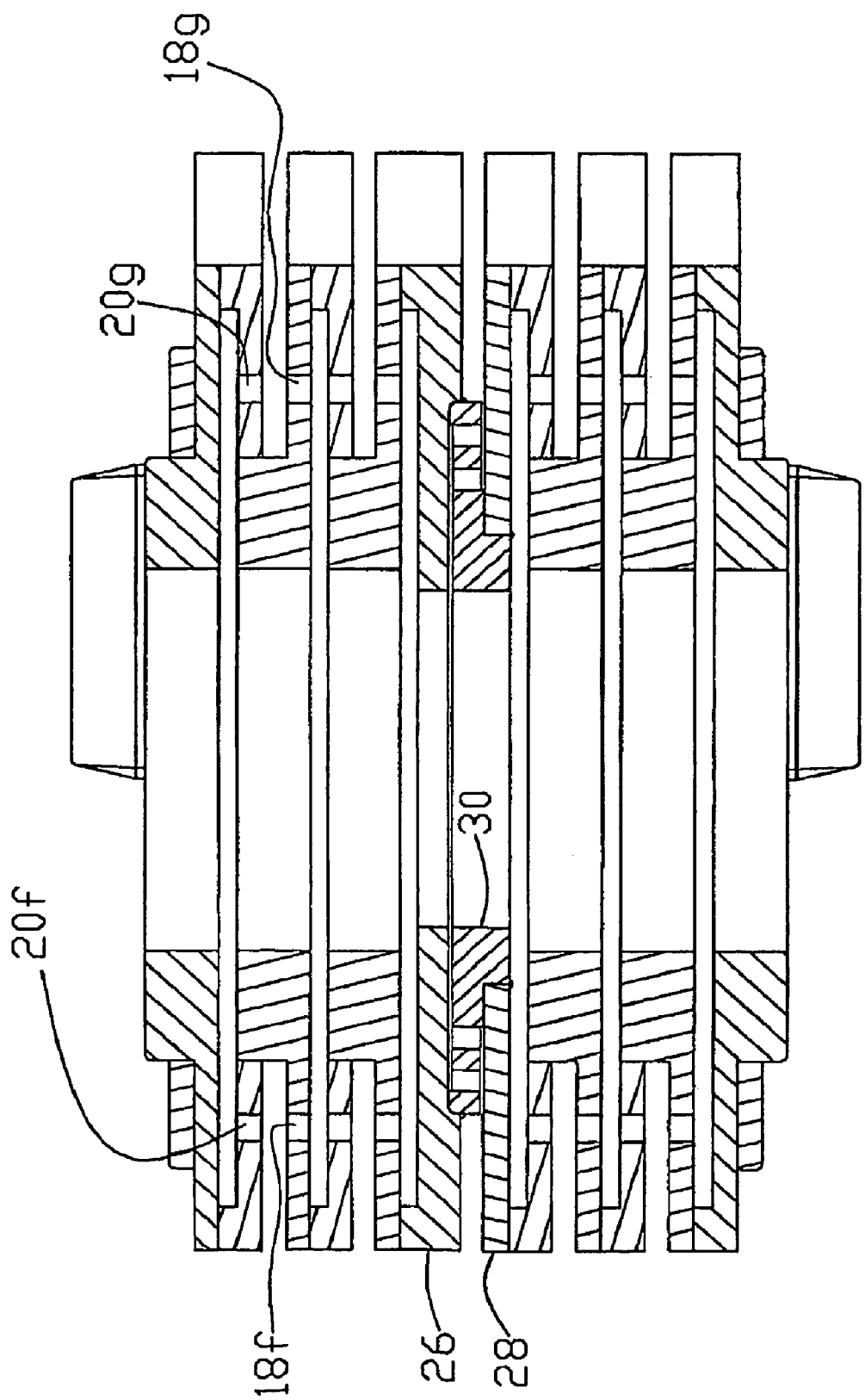
FIG. 18 is a cross-sectional view of the device of FIG. 3 incorporating the rotational dampening subassembly taken along lines 18-18.

FIG. 18 is a side cross-sectional view of the device of FIG. 17 showing the flexion slots 18f, 18g, and 20f, 20g.

Figure 19:
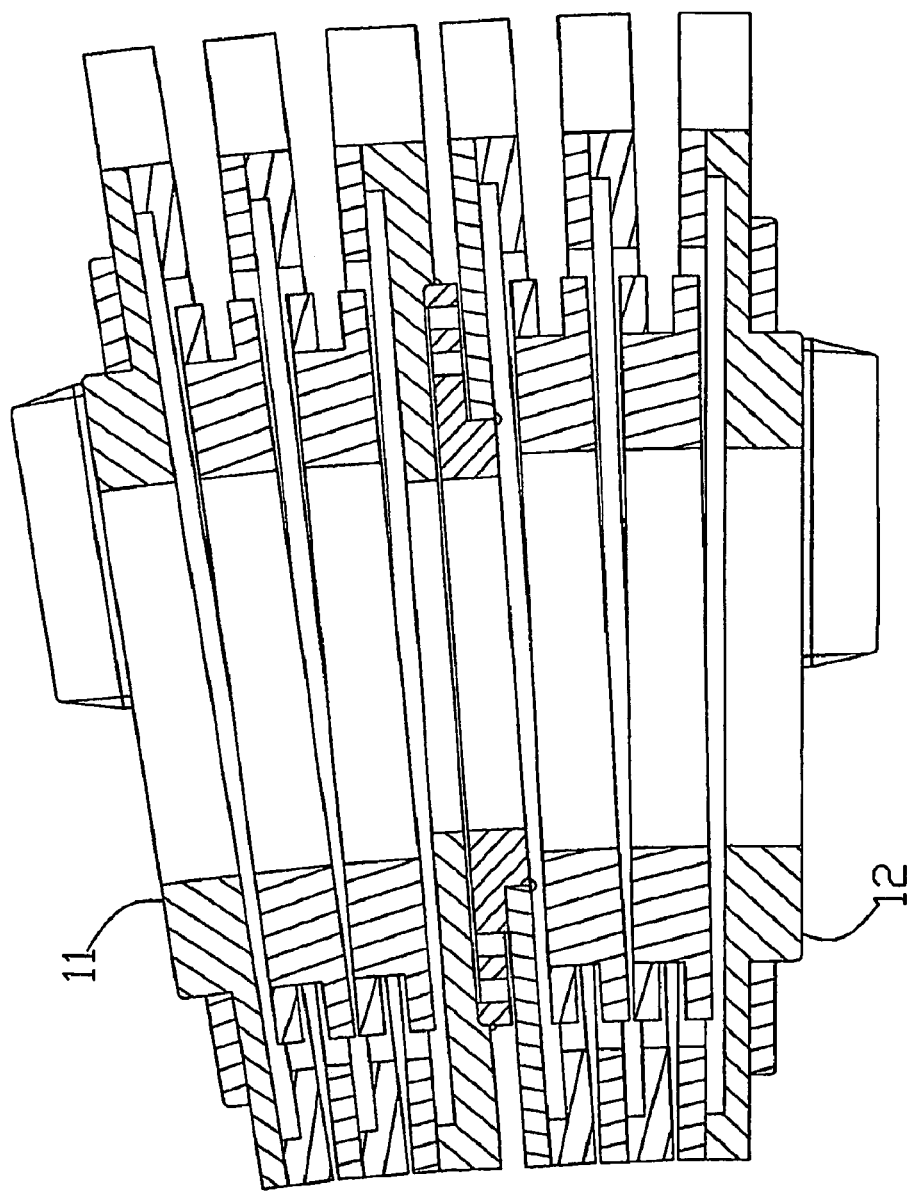
FIG. 19 is the same cross-sectional view as FIG. 17 showing articulation of the device.

FIG. 19 is a side cross-sectional view of FIG. 17 illustrating articulated/pivoted motion between the end plates 11 and 12.

The overall height h (FIG. 10) of the intervertebral motion restoring device will depend upon its selected location and the patient's anatomy. As an example, h should be within the range of about 0.19 to 0.315 inches and 0.315 to 0.8 inches for use in the cervical or thoracic and lumbar regions, respectively.

As a further example for a height h of 0.565" the spaces 22 and 24 (FIG. 5) are preferably 0.015 and 0.012 inches, respectively. Such a device may have a width w and a length l (FIGS. 4 and 5) of about 1.0 and 1.4 inches, respectively.

Figure 21:
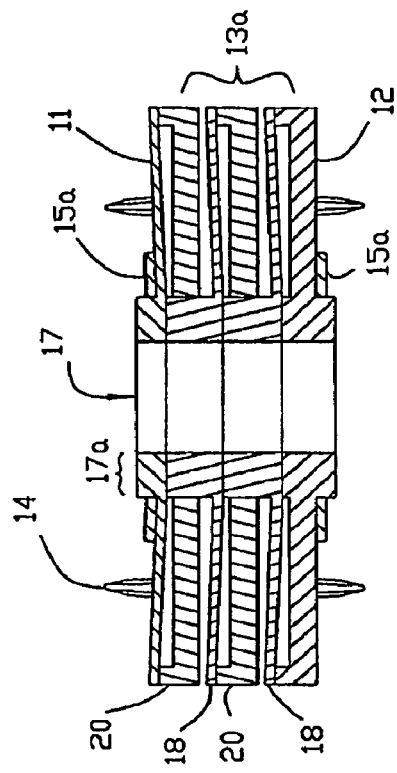
FIG. 21 is a cross-sectional view showing the disc in a vertically compressed mode.
Figure 20:
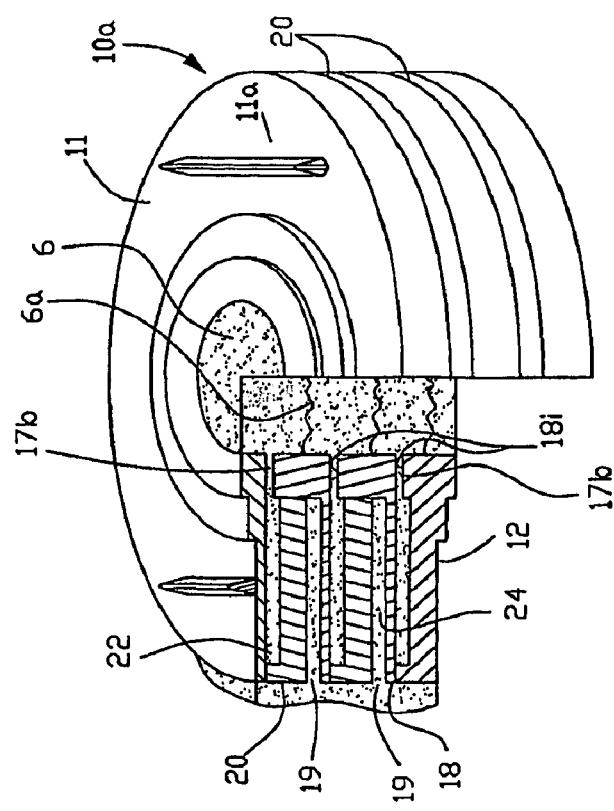
FIG. 20 is a perspective view, partially broken away, of a modified disc similar to the disc of FIG. 3 showing the migration of bone within the central core and soft tissue within the soft tissue channels or voids.

A slightly modified disc is shown in FIGS. 20 and 21 in which corresponding components are identified with the same numerals.

The difference between the intervertebral disc of FIGS. 20-21 and the disc described in FIGS. 3-12 (except for the number of intermediate plates 18, 20) is the addition of the extensions 18i of central portions of plates 12 and 18 which; when the spacer is in the unstressed condition, form gaps 17b in the central section. These extensions serve as a stop means to limit the compression and axial articulation of the support structure without completely closing the channels 22 and 24, preserving the fatigue life of the disc.

As an example, for a support structure 13' having a height of about 5 mm, the gaps 17'b between the extensions 18i and the adjacent plates may be about 0.015" while the channels 22 and 24 may have a height of about 0.020". This difference in the dimensions of the gaps versus the height of the channels allows the spacer to be completely compressed (i.e., along the longitudinal axis) without completely closing the channels 22 and 24 by providing stop means, i.e., contact locations along the central section 17a, to accommodate abrupt loads and to alleviate fatigue failure which may otherwise occur as a result of repetitive loads. This also prevents complete soft tissue compression within the voids 22 and 24 and allows for additional disc bending when fully compressed.

FIG. 20 illustrates the infiltration of soft tissue 19 within the channels between the plates and some migration of a bone strut 6 within the core 17 forming nonunions at locations 6a. The soft tissue infiltration in the large areas within the channels results in a nonlinear increase in stiffness of the spacer as the load is increased thereby simulating the response of a natural disc. The design of FIGS. 20 and 21, as well as the designs shown in subsequent figures have the ability to openly integrate with varying combinations and densities of bone and soft tissue, thus producing a hybrid device made of both inorganic (metal or polymer) and organic (cellular tissue and/or bone) materials. The advent of continuous or discontinuous bone struts through the device as discussed previously will yield a device which is stable, yet more flexible, than a device relying on rigid fusion, thus providing the capability of energy absorption. It is to be noted, however, that bone struts are not required to produce a positive result. Soft tissue, will in time, infiltrate the voids producing a device which will more closely mimic a natural disc. This will be explained in more detail in conjunction with FIG. 22.

FIG. 21 illustrates the disc completely compressed by a vertically oriented or axial load with the gaps 17'b closed. The spacer in such a collapsed mode will still accommodate a lateral bending action, i.e., about the longitudinal axis.

Figure 22:
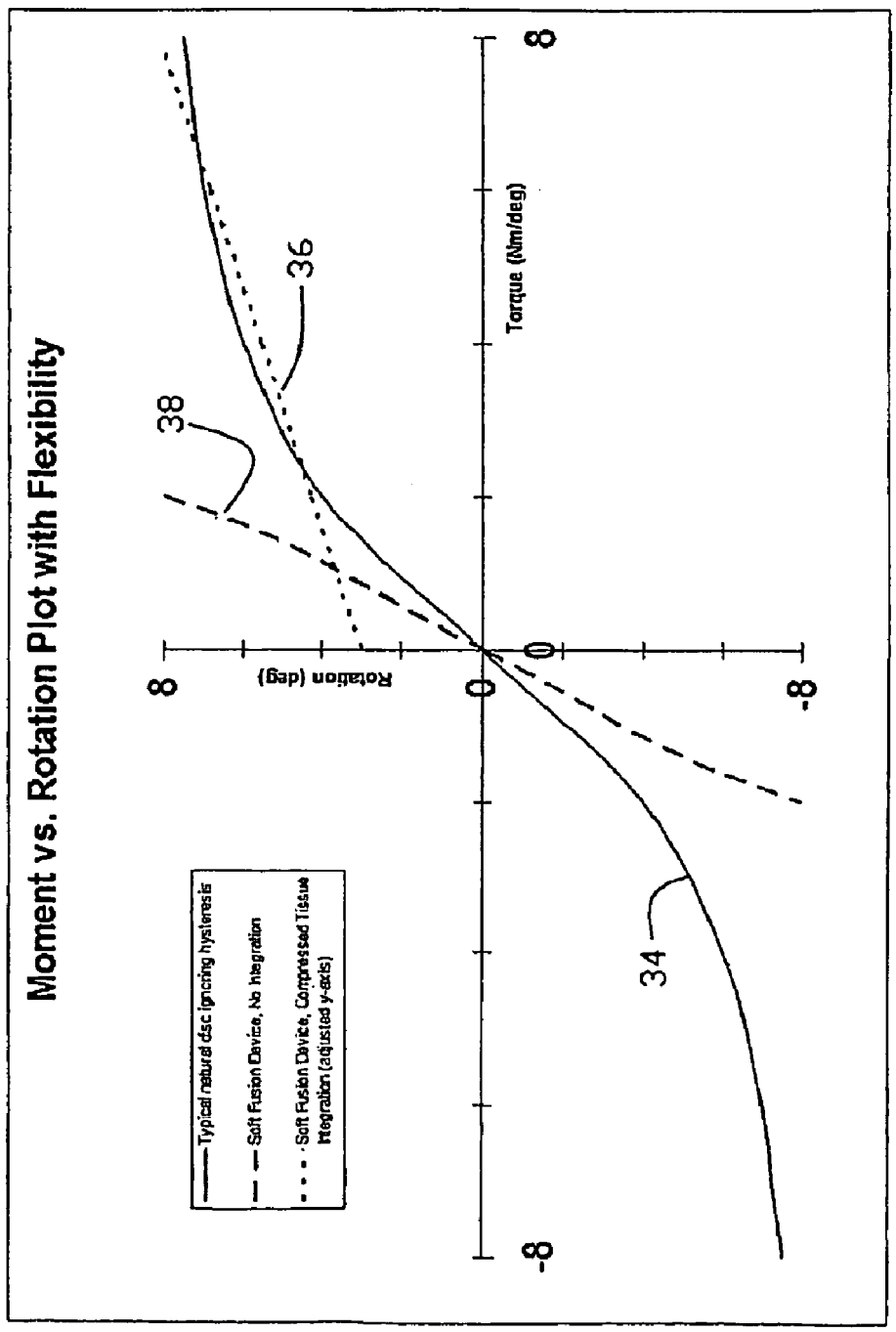
FIG. 22 is a graph showing a typical moment versus rotation plot of a natural disc versus that of a computer model of the artificial disc of FIG. 20 when bone and tissue have penetrated the voids as illustrated in FIG. 20.
Figure 26:
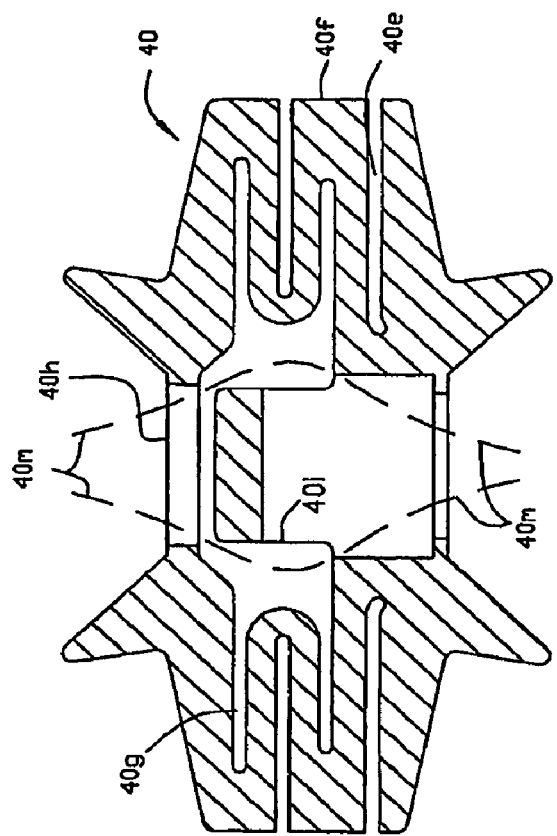
FIGS. 25 and 26 are cross-sectional views taken along lines 25-25 and 26-26, respectively in FIG. 23.
Figure 25:
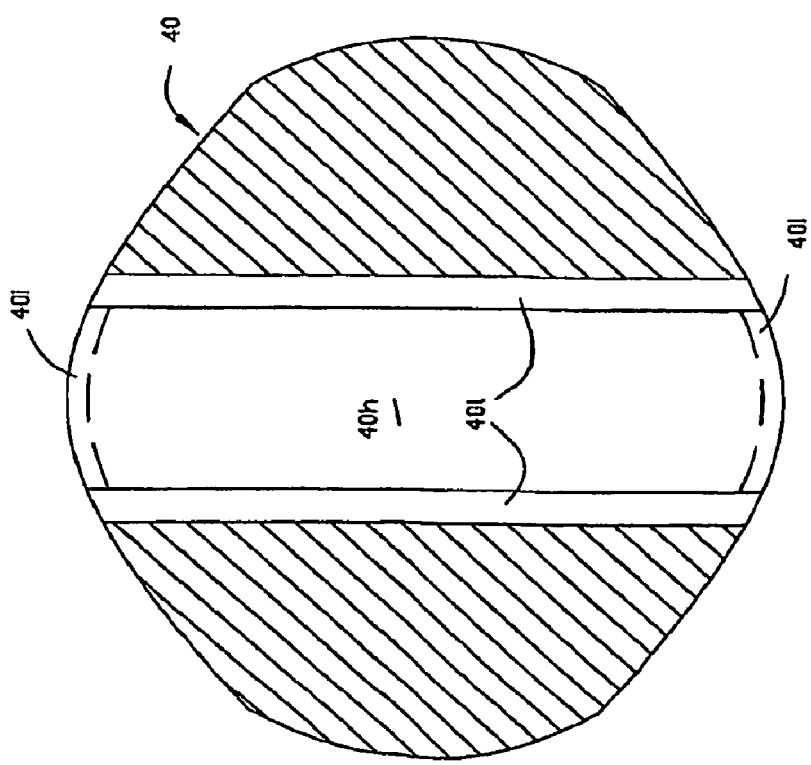

FIG. 22 is a graph showing lumbar-disc moment in Newton meters/degree verse rotation plot in degrees (around a horizontal axis) of a typical natural disc (curve 34), hysteresis ignored. This response of a natural disc is illustrated by Dr. Spenciner D. et al., in The multidirectional bending properties of the human lumbar intervertebral disc. Spine J. 2006 May-Jun. 6(3):348-57. The slope of the curve at any point represents the disc flexibility. Curves 38 and 36 represent the theoretical response of a computer model of the intervertebral spacer of FIGS. 20 and 21. It is to be noted that the response of an actual mechanical disc made in accordance with this invention may vary from that shown by the curves. For small displacements and loads, soft tissue integration within channels 22, 24 will provide little resistance and thus the device will have a greater flexibility as shown by curve 38. As the motion and loads increase, the soft tissue will become increasingly compressed and strained. Due to soft tissues' nonlinear mechanical properties, the soft tissues will provide an increased degree of resistance with each increase in motion as is illustrated by curve 36. The actual hybrid Soft Fusion device flexibility curve will include a curve similar to curve 38 and transition to a curve similar to curve 36.

The area of the bone accommodating core 17 or cores should not exceed about 35% and preferably less than about 25%, (e.g., about 10-20%) of the total area of the disc facing the separated vertebral bodies, i.e., in a horizontal plane. The size of the disc and bone strut opening(s) therein will depend upon the size of the vertebral bodies to be supported. As an example, the total area of the openings should have a diameter, if circular, or equivalent dimensions if non-circular, within the ranges of 0.1 to 0.6, 0.1 to 0.7, and 0.2 to 0.7 inches in diameter for the cervical, thorax, and lumbar regions, respectively.

An alternative embodiment of an intervertebral or hybrid disc designed primarily for the cervical region, is illustrated in FIGS. 23-26 wherein the disc 40 is formed with L upper and lower surfaces 40a and 40b, respectively and a central elongated generally elliptical open core 40c, partially obstructed by a bone integration diversion plate or beam 40h to be described. Keels 40d extend outwardly from the upper and lower surfaces to aid in securing the spacer between the supported vertebral bodies. The spacer includes generally planar semicircular soft tissue integration channels 40e extending inwardly from the exterior or peripheral wall 40f to a location short of the open core 40c. Generally semicircular tissue integration channels 40g are interleaved with the channels 40e and extend outwardly from the core 40c to a location short of the exterior wall. The centrally located bone diversion beam 40h extends laterally across the core 40c below the upper surface 40a as shown more particularly in FIGS. 9 and 10.

The beam is held in place by downwardly extending legs 40i which are formed with or otherwise secured to the lower peripheral wall at 40j (FIG. 23). The ends of the beam 40h are arranged to abut the opposed ends 40k of the top of the spacer at the ends of the open core to limit the compression (and vertical articulation) of the spacer when subjected to excessive loads. It is to be noted that the number and configuration of the tissue integration channels may vary.

The bone diversion bar 40h creates channels 40l (FIG. 25) which promote relatively narrow bone growth along lines 40m to result in soft fusion. The cross-sectional area at the channel 40l is preferably within the range previously discussed.

Another alternative hybrid intervertebral disc 42/44 is illustrated in FIGS. 27-29 which includes an upper and lower section 42 and 44, respectively. The upper section 42 includes a top surface 42a, an exterior peripheral surface 42b, an inner surface 42c surrounding an open cylindrical core 42d. A ring-shaped inner cavity 42e, open at the lower end and forming an arch 42f at the upper end is formed in the upper section. The upper section is also formed with a helical ¾-1½ turn slot (or channel) 42g extending from the inner to the outer surfaces and through the cavity 42e as shown in FIG. 29. The slot is formed with stress relieving end openings 42h. The spiral slot 42g accommodates limited rotation about a vertical axis (e.g., about 3 degrees) and compression. The voids between the post and the cavity as well as the spiral slots to accommodate the infiltration of soft tissue. The hollow core 42d will accommodate the infusion of bone and or soft tissue growth.

The inner surface 42i (FIG. 29) facing the cavity 42e is threaded at 42k for receiving the lower section 44. The lower section 44 is formed with an upwardly extending annular or donut-shaped post 44a extending into the cavity 42e. The lower section includes male threads 44b offset from an inner wall 44c thereof which threads cooperate with the threads 42k to join the lower section to the bottom of the upper section as shown. An outwardly extending flange 44d abuts an annular shoulder 42l to allow a surgeon to preset the compression of the spacer via the threads 42k/44b as will be apparent to those skilled in the art. The bottom surfaces 44d and 42n are arranged to engage the face of the lower vertebral body.

The abutting surfaces 44d and 42l will only transmit axial compressive and bending loads. This connection will only allow distractional, rotational and translational loads to be carried by the inner spring (formed by the inner cylindrical section 42j), softening the device in those motions. Excessive translations will contact surfaces 44c and 42i and then load the outer spring (formed by the outer cylindrical section 42m). The structure forming the inner and outer springs is discussed in conjunction with FIG. 30.

The upper end 44e of the post 44a is arranged to abut the top 42f of the cavity to limit the compression and vertical articulation of the device.

FIG. 29a illustrates a slight variation of the disc of FIGS. 27-29. In this variation the threaded connection 42k/44b has been replaced with a weld at 44'f and the addition of a small gap 42'm, e.g., 0.010" to 0.040" between abutting surfaces 42'l and 44'd. As a result the inner spring, formed by the spiral slot 42'g in the inner wall 42'n, takes substantially all of the compressive load until the gap 42'm is closed. Then the outer spring, formed by the slot in the outer wall 42'o, assists with resisting the forces. This gap 42'm also serves another purpose. The outer spring accommodates only compressive loads (including bending), but not extraction or rotation about the longitudinal axis X-X. This arrangement softens the spacer for both loading conditions. The outer spring will also not absorb any translation until the gap 42'm is closed. This will allow motion more closely simulating that of a natural disc.

Figure 31:
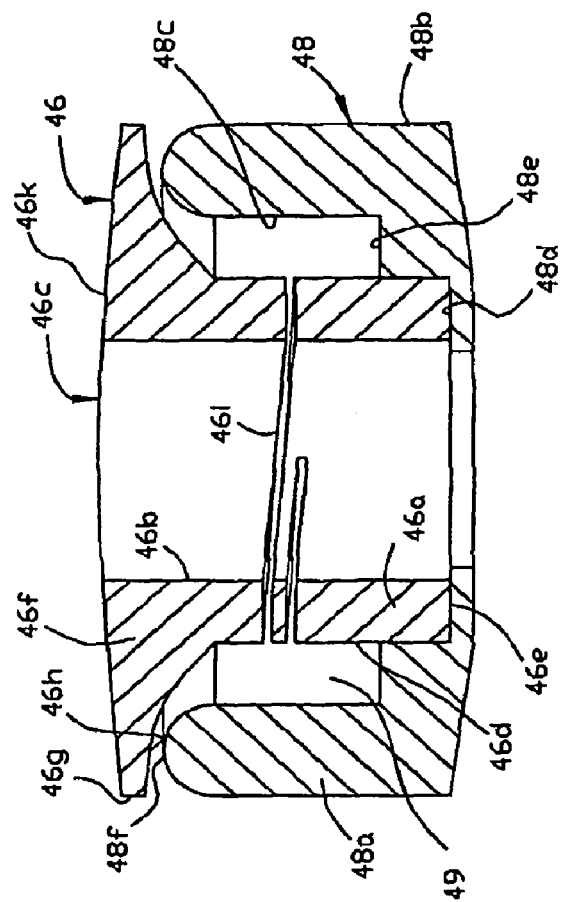
FIGS. 30 and 31 are side elevational and cross-sectional views of another interbody disc.
Figure 30:
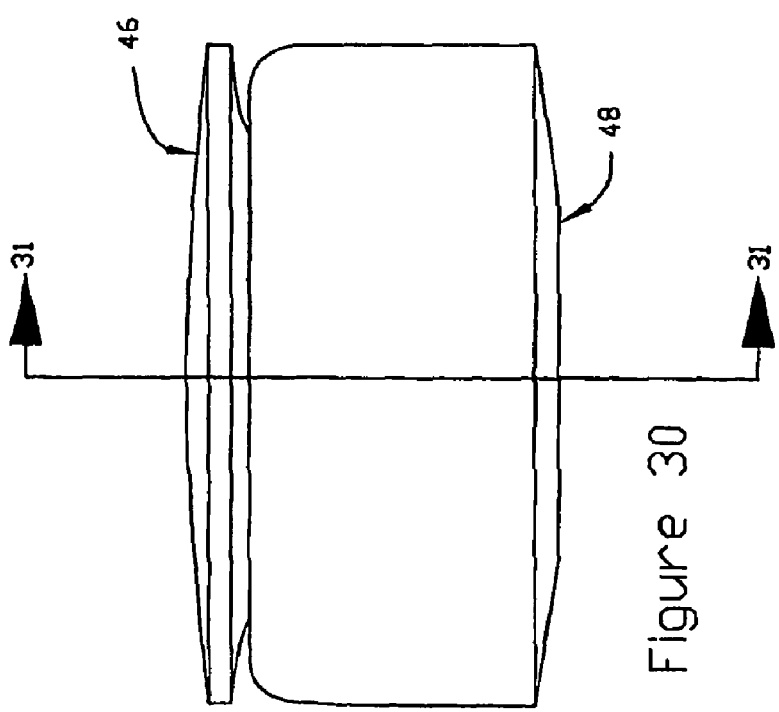

Another embodiment of a hybrid intervertebral disc 46/48 is illustrated in the side elevational and cross-sectional views of FIGS. 30 and 31 with the understanding that the top plan view of the disc would be similar to that shown in FIG. 27. This spacer is formed with an upper section in the form of a cylindrical hub 46a, having an inner surface 46b surrounding an open central core 46c and an outer surface 46d. The hub extends upwardly from a flat bottom 46e to an outwardly flanged head portion 46f to a rim 46g. The lower section 48 is in the form of an annular post 48a having exterior and interior surfaces 48b and 48c, respectively, with the inner surface stair-stepped inwardly to form shelves 48d and 48e with the shelf 48e abutting the bottom 46e of the upper section. The convex, i.e., semicircular, upper end 48f of the post is arranged to abut the inner surface 46h of the flanged head 46f to stop the articulation of the hub when the device is subjected to excessive loads, while allowing limited rotation. The hub is formed with a ¾-1½ turn channel or slot 46i. The top and bottom surfaces 46k and 48g are arranged to engage the faces of the respective vertebral bodies to be supported.

The voids formed by the spinal slot and the space 49 between the outer and inner surfaces of the hub and the annular post, respectively, provide soft tissue ingrowth locations. The open core will allow bone and/or soft tissue ingrowth.

FIGS. 32-34 illustrate an additional embodiment of the present invention in the form of an inner cylindrical member 50 having an open core 50a adapted for bone and/or soft tissue ingrowth and a centrally located 1-1½ turn helical slot 50b adapted for soft tissue ingrowth. An annular outer member 52 includes a bottom portion 52a with its inner surface 52b secured, e.g., by welding, to the outer surface 50c of the inner member.

The bottom 50d of the inner member forms an annular shelf 50e which sits under the bottom of the outer member portion 52a as shown. The top portion 52c of the outer member is secured at its inner surface 52d by welding, for example, to the outer surface along the top portion of the inner member. The top and bottom portions 52a and 52c are formed with concave mirror image surfaces 52e and 52f between which an articulation stopping ring 54 (circular in cross section), is positioned. The upper and lower surfaces of the 50/52 disc serve to engage the faces of the supported vertebral bodies.

The ring is preferably free floating within the space created by the surfaces 52e and 52d and smaller in diameter than the distance between such surfaces to allow the inner member to provide a limited amount of articulation, i.e., compression before making contact with both surfaces to stop the articulation resulting from an excessive load. The helical slot and the area surrounding the ring 54 are adapted for soft tissue ingrowth while the open core is adapted to accommodate bone and/or soft tissue ingrowth.

Figure 36:
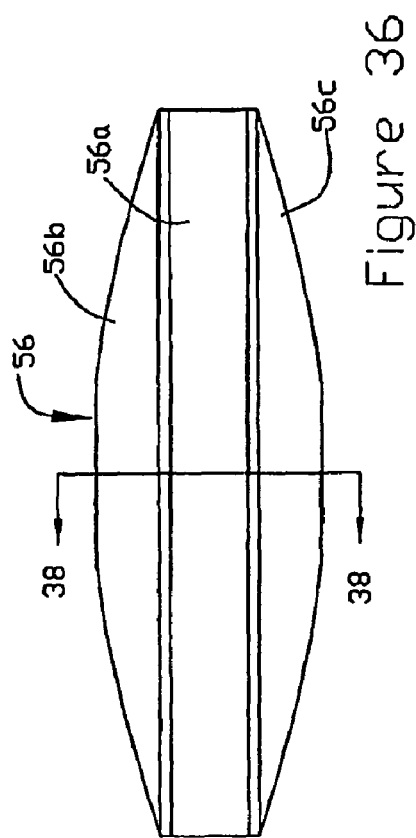
FIGS. 35-37 are top plan, side elevational and cross-sectional views of another disc embodiment.
Figure 37:
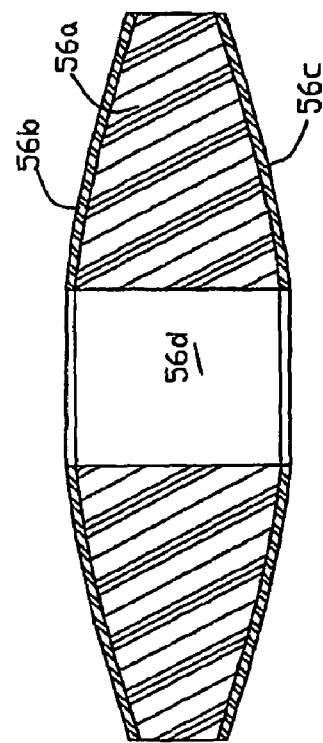
Figure 35:
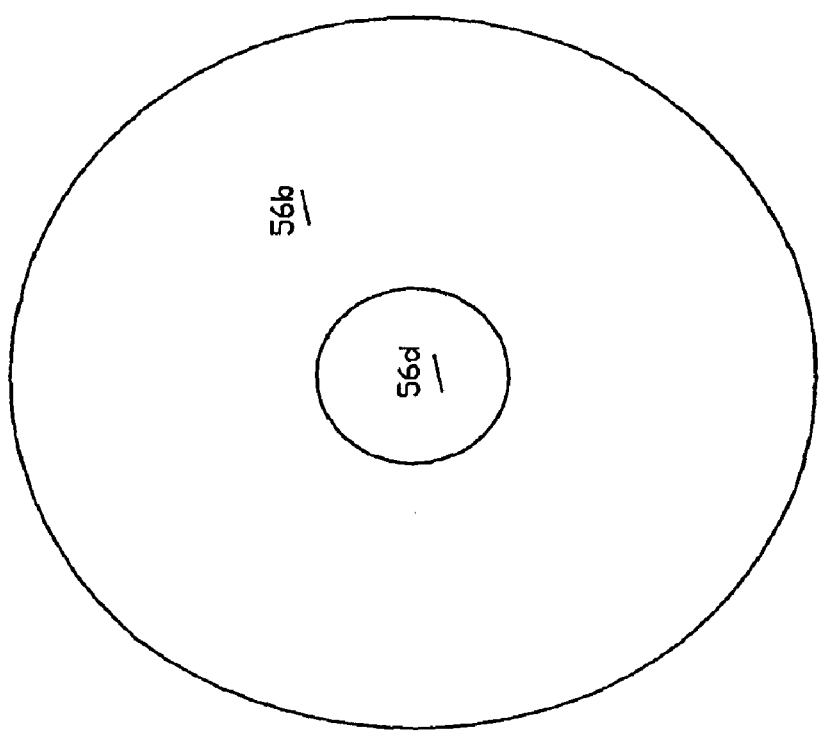

FIGS. 35-37 illustrate a modified disc 56 in which a suitable polymer 56a is enclosed by end plates or discs 56b and 56c with an open central core 56d for accommodating a bones strut to provide soft fusion. The spacer must have sufficient strength and stiffness (as discussed earlier) to support the adjacent vertebrae in their natural separated setting and yet under normal loads compress sufficiently to disrupt the bone struts within the open core to form one or more fibrous nonunion joints.

Figure 42:
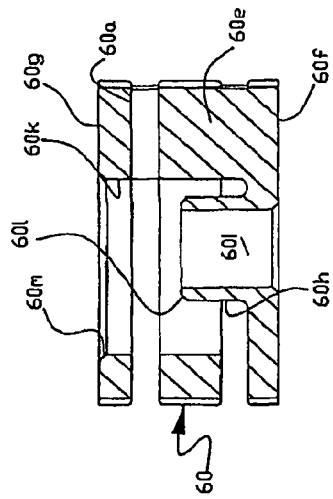
FIGS. 38-42 are top plan, side elevational, bottom, end and cross-sectional views, respectively, of a base component of an alternative two-piece disc.
Figure 41:
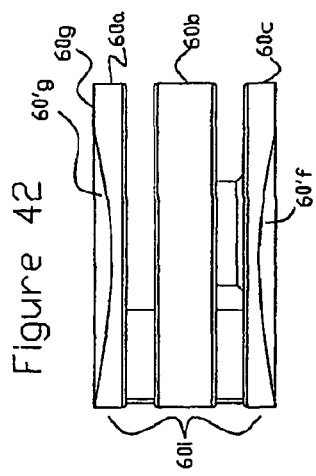
Figure 39:
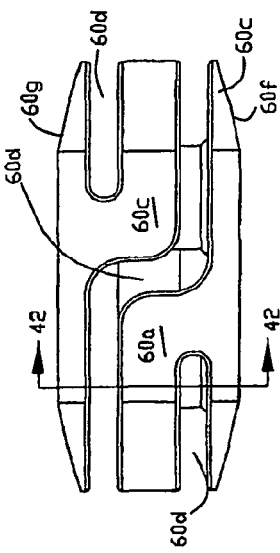
Figure 38:
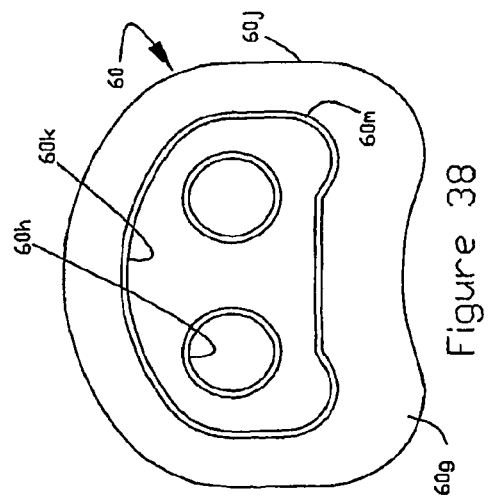
Figure 40:
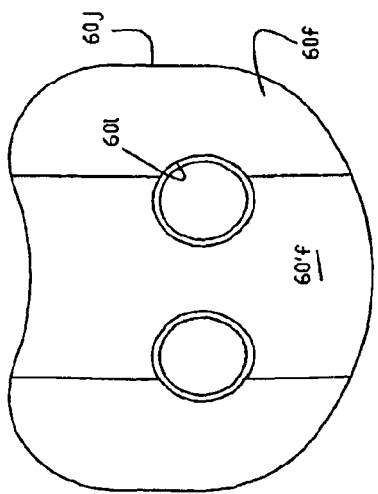
Figure 67:
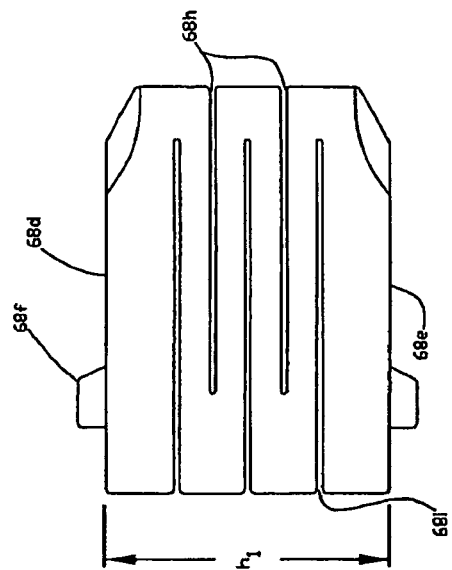
FIGS. 65-68 are top plan, side elevational, end and cross-sectional views of another embodiment of an anterior disc.
Figure 66:
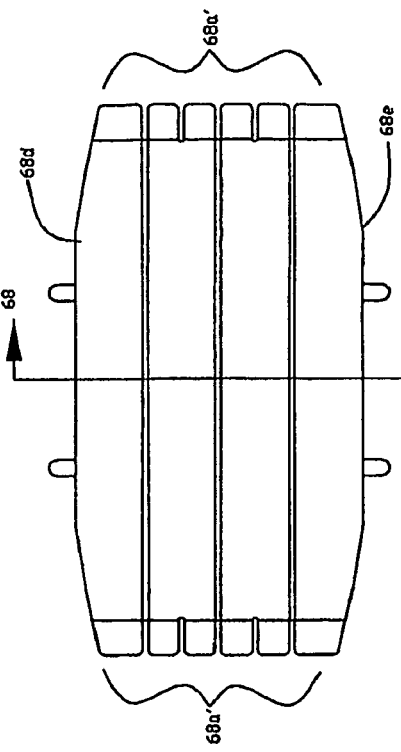

An additional two part disc, suitable for creating soft fusion, is illustrated in FIGS. 38-51 where FIGS. 38-42 show the bottom or base component 60, FIGS. 43-47 show the top or upper component 62, and FIGS. 48-51 show the assembled disc. The base component comprises upper and lower rings 60a and 60c separated via a partial ring 60d which is joined by bridged portions 60e to the upper and lower rings, as shown (FIGS. 42, 43). A serpentine slot 60d extends through the base component accommodating the infusion of tissue and allowing limited axial and rotational motion between the upper and lower rings. Bottom and top walls 60f and 60g include centrally located concave portions 60'f and 60'g for engaging the exposed surfaces of the supported vertebral bodies. A pair of tubular posts 60h, defining open cores 60i, extend upwardly from the lower ring 60c. The outer surfaces of the rings define a peripheral wall 60j (FIG. 41) conforming generally to the kidney shape of the face of the vertebral bodies to be supported. A central section 60k surrounding the posts extends upwardly from the lower ring to an open top. A beveled surface 60m is formed at the upper end of the central section to provide a seat for a plate 62a of the top component to be described. In addition, an annular bevels 60l is formed on the outer surface at the top of tubular posts as shown to mate with a matching bevel on nipples carried by the upper component to limit axial motion as is illustrated in FIG. 51.

The upper component 62, shown in FIGS. 43-47, includes a cover plate 62a contoured to mate with the open end of section 60b via a matching beveled surface 62b. The plate is formed with circular openings 62c from which depend tubular nipples 62d defining stepped openings, the upper portion 62e thereof transitioning to a lower portion 62f via a bevel 62g. The inner surface of the lower portion 62f is arranged to encircle the outer wall of a respective post 60h with the bevel 62g being arranged to engage the post bevel 62l to limit the axial travel of the disc as is illustrated in FIG. 51. The posts 60h and the supplier 62d are sometimes referred to as an appendage The base and upper components as assembled are secured together along the beveled surfaces 60m and 62b, for example, by a TIG welding operation to fill in the area between the beveled surfaces. See FIG. 48. In the unlikely event of flexural element failure, the device will collapse and allow the beveled edges 62g and 62l to contact and center the device, limiting motion while stabilizing the disc.

The aligned openings 60i and 62e form bone accommodating channels to enable pseudoarthosis struts to form therein, which along with the mechanical characteristics of the disc, provide soft fusion as discussed.

FIGS. 52-64 illustrate another two part disc in which FIGS. 52-56 show an upper (or inside) component; FIGS. 57-61 show a lower (or outside) component and FIGS. 62-63 show the assembled unit. The upper component 64 also comprises an upper and lower ring 61a and 64c with an intermediate partial ring 64b, separated from the upper and lower rings, by a serpentine tissue accommodating slot 64d and joined thereto by bridged segments 64e. As was discussed with respect to FIGS. 38-50 the slot accommodates the infusion of soft tissue and allows limited axial and rotational motion. A top wall 64f includes keels 64g and a hollow post 64h (defining a bone accommodation channel 64i) extends downwardly from the central section of the top ring and defines a notched keyway 64j in the bottom peripheral wall for cooperating with a mating upwardly projecting key formed on encompassing sleeve of the lower or outside component to be described for limiting the rotational mobility of the disc.

The lower component 66, shown in FIGS. 57-61, is formed with a base 66a supporting a pair of outwardly projecting spaced keels 66b, offset 90 degrees from the upper component keels, as is shown in FIG. 64 and an upwardly extending sleeve 66c arranged to surround the post 64h in the assembled condition. The base includes a radially inwardly projecting key 66d for mating with the keyway 64j. See FIG. 64. In the assembled condition, the two components are secured together, e.g., by welding the outer edge 66e of the base 66a to the inner edge 64k of the ring 64c as is indicated at 65 on FIG. 64.

Figure 65:
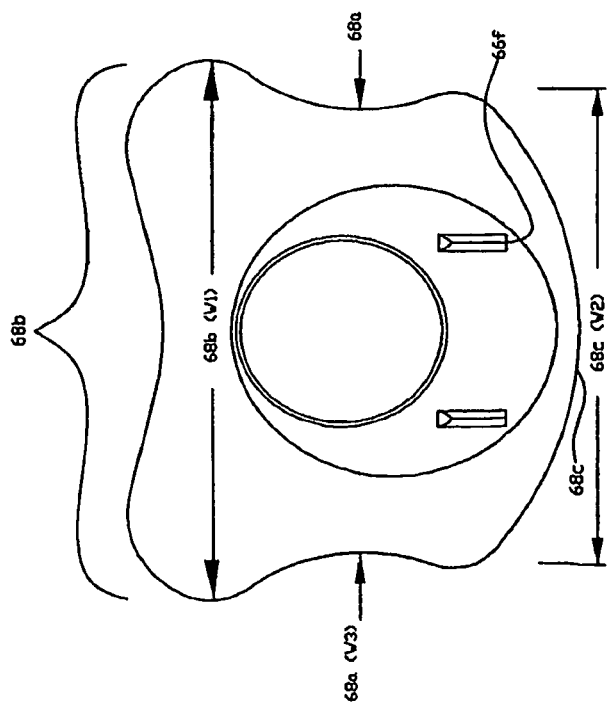
Figure 68:
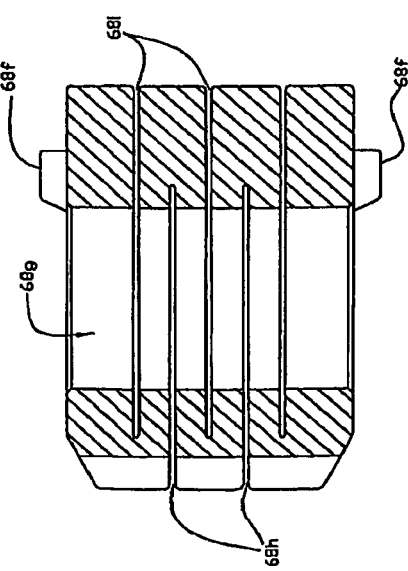
Figure 69:
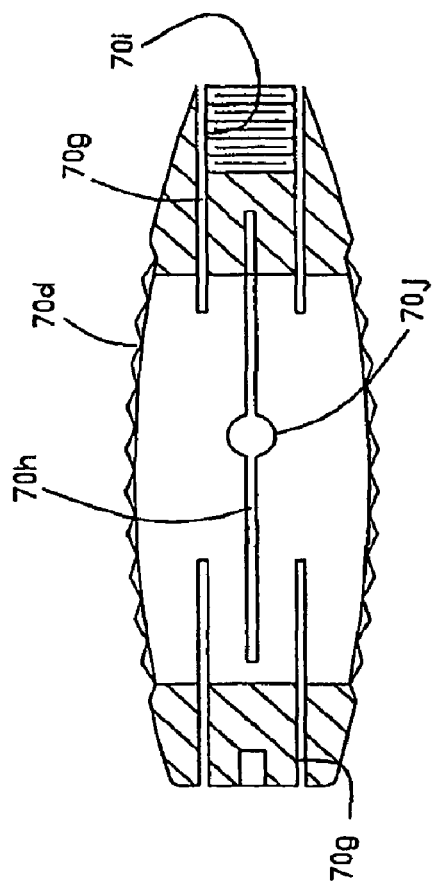
FIGS. 69-72 are top plan, side elevational, end and cross-sectional views of a posterior disc in accordance with the invention.
Figure 70:
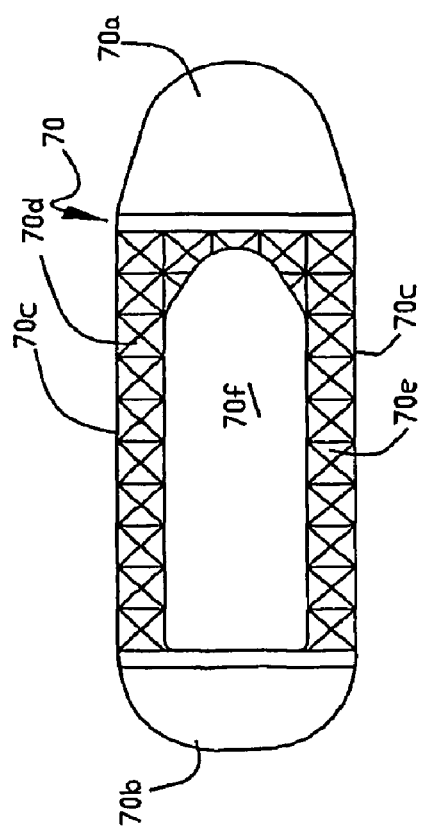
Figure 71:
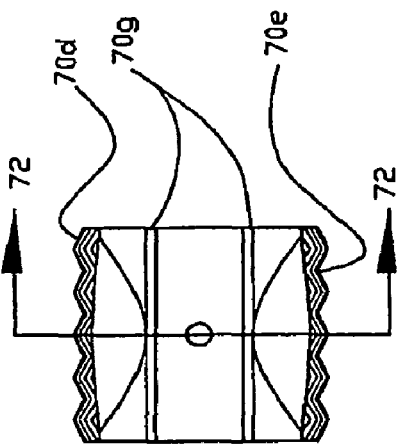
Figure 72:
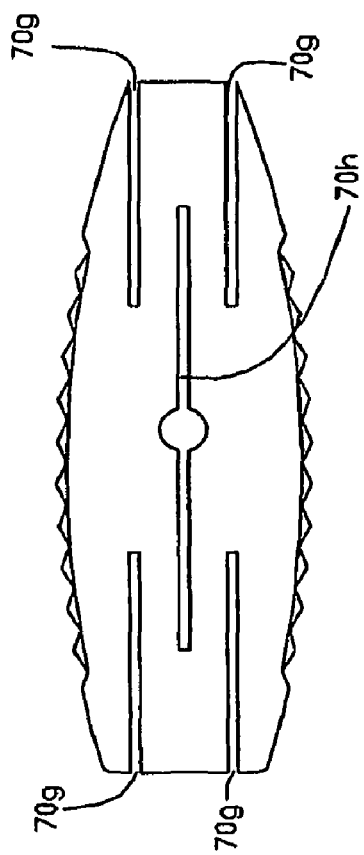

FIGS. 65-68 illustrate another embodiment of an anterior disc 68 in the general shape of a natural disc (e.g., kidney-shaped) as shown with pinched sides forming a relatively narrow midsection 68a, resulting in expanded or widened front and back wall areas 68b and 68c, respectively (in a horizontal cross-sectional view), and a narrower midsection (of the side walls 68'a) as is shown in FIG. 65. The disc further includes top and bottom surfaces 68d and 68e and keels 68f extending outwardly from the top and bottom surfaces. A centrally located core 68g accommodates bone growth to form living, not completely formed, bone struts. Interleaved lateral horizontal slots or slits 68h and 68i extend from the front and back walls, respectively, through the open core, as shown, to accommodate axial and binding loads and the infiltration of soft tissue. The slots 68h and 68i terminate a short distance from the back and front walls, respectively. As an example the widths $W_1$, $W_2$ at the front and rear expanded wall areas 68b and 68c and $W_3$ at the narrow waist wall area, may be about 1.4, 1.2, and 0.95 inches, respectively, as is illustrated in FIG. 65. With the above dimensions in mind, the 68h and 68i slots may have a depth of about 0.012 to 0.014 inches and terminate about 0.250 and 0.135 inches from the back and front walls, respectively. The height $h_1$ of the disc will vary depending upon its intended location. For example, $h_1$ may vary between about 0.2 to 0.38 inches. Also, the number of slots may and probably will vary depending upon the height of the disc with the shorter discs having three slots while the higher discs will have five slots, for example.

As the disc flexes the widened front and back sections adjacent wall 68*b* and 68*c* overlying the slots, transition from level to level (vertically) compressing the slots these wall areas tend to widen out. This action allows these wider areas to transition the load to the next bend or level without fatiguing the disc material. By the same token, the narrower midsection 68*a* allows more bending, but still without causing fatigue failure. The collapse of the slots with or without soft tissue infused therein serves to limit the compression of the disc due to excessive loads inhibiting fatigue failure.

FIGS. 69-72 illustrate an intervertebral disc 70 designed for posterior implantation. The disc (like the previously described discs) is formed of a suitable biocompatible material, such as Ti, stainless steel, etc. The disc includes a bulbous nose section 70*a*, with a threaded blind bore 70*a* for receiving an implantation tool (not shown) and a tail section 70*b* with side sections 70*c* extending between upper and lower vertebral body engaging surface 70*d* and 70*e*. A central bone growth accommodating opening 70*f* is located between the side sections. The disc is elliptically shaped in an elevational and cross-sectional view as is shown in FIGS. 53 and 54. The disc is formed with fore and aft horizontal tissue accommodating slits or channels 70*g* which extend through the nose and tail sections and partially through the side sections as shown. A centrally located slit 70*h* extends through the side sections and into the nose section. The slits allow limited axial and bending motions. A centrally located aperature 70*j* accommodates the insertion of a wire for forming the slot 70*h* during the manufacturing operation The vertebrae engaging surfaces 70*d* and 70*e* are roughened, i.e., forming projecting pyramids, to provide bone attachment friendly surfaces.

Figure 73:
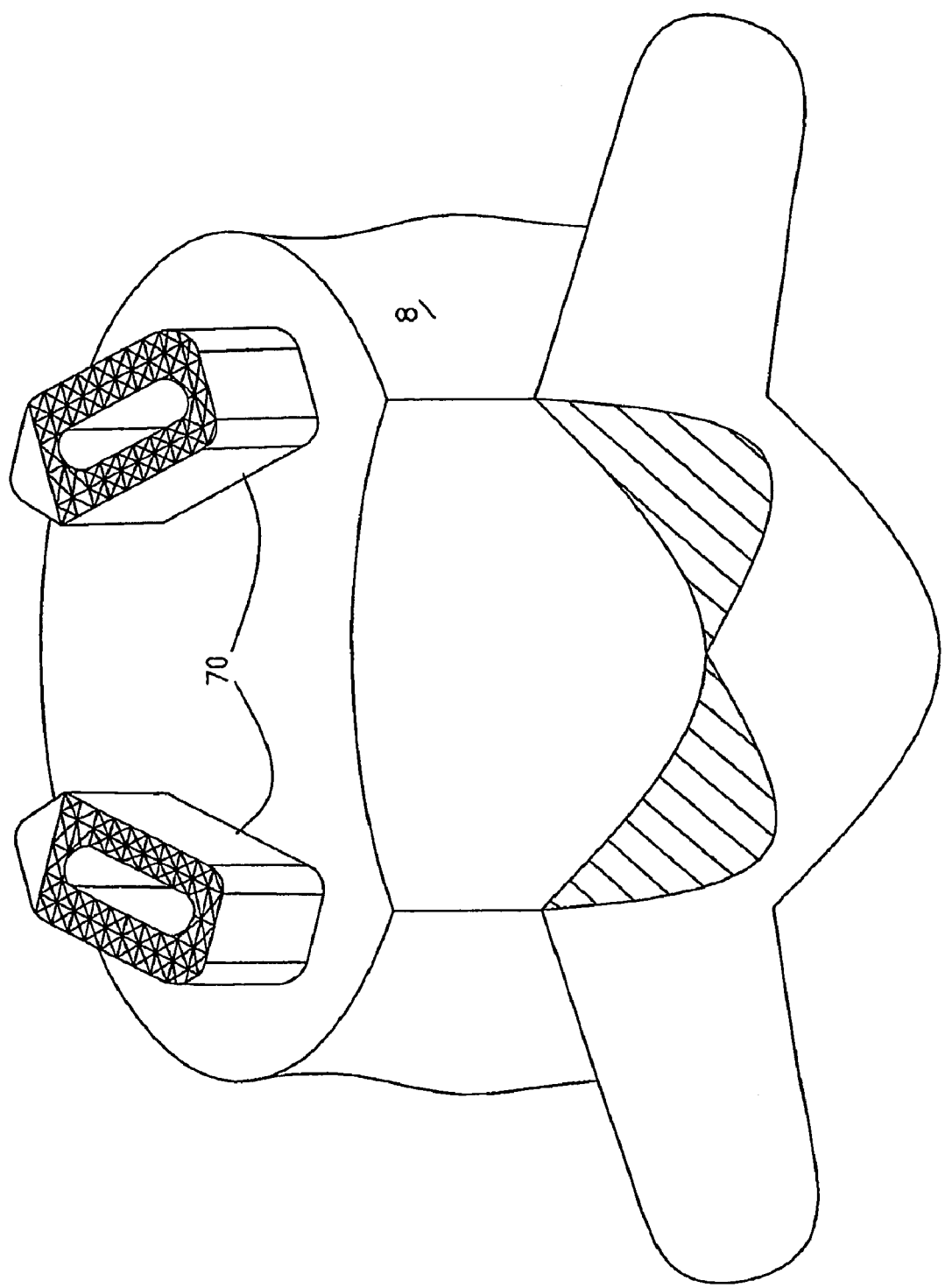
FIG. 73 is a perspective view of two of the discs of FIGS. 69-72 placed on the exposed face of a lower vertebral body.

FIG. 73 illustrates the placement of two of the posterior discs 70 on the face of an underlying vertebral body 8. As pointed out previously, the voids between and outside of the discs may be filled in with a material inhibiting bone growth.

FIGS. 74-78 illustrate an additional intervertebral disc 72 designed for posterior insertion which, like the anterior disc of FIGS. 65-68, is formed with pinched side walls 72*a* at the center thereof and expanded or widened intermediate side wall sections 72*b* (adjacent the front and rear end walls 72*c* and 72*d*) for accommodating higher loads in the wider intermediate sections and increased bending along the center section. As an example, with an overall length of about 1.0" and a height h of about 0.40", the widths $W_3$ of the widened areas may be about 0.48" and the center narrower area $W_4$ about 0.36" and the width $W_5$ of the end 72*d* is about, 0.25". The disc defines a centralized elliptically shaped bone channel 72*e* with slots 72*f* and 72*g* extending from the front and back, respectively, through the side walls and core 72*e*, but terminating short of the rear and front walls, as shown. The outlet of the slots are tapered at 72*h* to accommodate bending stresses. The top and bottom surfaces 72*i* and 72*j* are formed with grooves 72*k* to enhance bone attachment. A threaded blind hole 72*l* is adapted to receive the threaded end of an insertion tool.

There has been described a prosthetic intervertebral disc for restoring the motion between the supported vertebral bodies while enabling the formation of pseudoarthrosistic continuous or discontinuous bone struts having nonunion locations within the disc and between the supported bodies thereby providing a state of soft fusion and optionally accommodating the infusion of soft tissue within generally planar spaces within the disc. The disc may take many structural forms as is illustrated by the accompanying drawings. Variations and improvements to the soft fusion/hybrid disc of the present invention will undoubtedly occur to those skilled in the art without involving a departure from the invention as defined in the appended claims.

The invention claimed is:

1. An intervertebral prosthesis comprising:
 a) an interbody disc having upper and lower surfaces for engaging the faces of adjacent vertebral bodies between which a natural disc has been partially or wholly removed, an exterior wall and one or more generally vertically oriented continuous or discontinuous bone channels of limited cross-sectional area to enable bone to form and fuse into one or more continuous or discontinuous struts between the vertebral bodies;
 b) the disc having a stiffness sufficient to support the vertebral bodies in their natural spaced relationship while allowing limited motion and being flexible enough when subjected to a predetermined load to alter the distance between the vertebrae engaging surfaces and transfer sufficient energy to the bone strut(s) to create one or more conditions of nonunion joints or pseudoarthrosis at locations along the strut(s); and
 c) the disc being further arranged to limit the movement thereof to an amount which is sustainable by the disc without resulting in fatigue failure during an anticipated life span, wherein the stiffness of the disc is within the range of about 50 to 4000 N/mm, wherein the total cross-sectional area of the bone channel(s) is about 35% or less of the total area of one of the disc vertebral body engaging faces,
 wherein the disc includes upper and lower rings separated by a partial ring joined to the upper and lower rings by a bridged portion defining a serpentine slot extending between the rings and an inner tubular appendage supported by one or both of the upper and lower rings, the appendage defining the bone channel(s), the disc further including cooperating means located on the upper and lower rings to limit the axial travel of the disc, the serpentine slot accommodating the infusion of soft tissue therein,
 wherein the tubular appendage comprises one or more downwardly extending tubular posts carried by the upper ring and cooperating upwardly extending nipple(s) carried by the lower ring, the post(s) and nipple(s) providing the means to limit the axial travel of the disc.

2. An intervertebral prosthesis comprising:
 a) an interbody disc having upper and lower surfaces for engaging the faces of adjacent vertebral bodies between which a natural disc has been partially or wholly removed, an exterior wall and one or more generally vertically oriented continuous or discontinuous bone channels of limited cross-sectional area to enable bone to form and fuse into one or more continuous or discontinuous struts between the vertebral bodies;
 b) the disc having a stiffness sufficient to support the bodies in their natural spaced relationship while allowing limited motion and being flexible enough when subjected to a predetermined load to alter the distance between the vertebrae engaging surfaces and transfer sufficient energy to the bone strut(s) to create one or more conditions of nonunion joints or pseudoarthrosis at locations along the strut(s); and
 c) the disc being further arranged to limit the movement thereof to an amount which is sustainable by the disc without resulting in fatigue failure during an anticipated life span, wherein the stiffness of the disc is within the range of about 50 to 4000 N/mm, wherein the total cross-sectional area of the bone channel(s) is about 35% or less of the total area of one of the disc vertebral body engaging faces, wherein the disc includes upper and lower rings separated by a partial ring joined to the upper and lower rings by a bridged portion defining a serpentine slot extending between the rings and an inner tubular appendage supported by one or both of the upper and lower rings, the appendage defining the bone channel(s), the disc further including cooperating means located on the upper and lower rings to limit the axial travel of the disc, the serpentine slot accommodating the infusion of soft tissue therein, wherein the tubular appendage comprises one or more downwardly extending tubular posts carried by the upper ring and cooperating upwardly extending nipple(s) carried by the lower ring, the post(s) and nipple(s) providing the means to limit the axial travel of the disc.

3. An intervertebral prosthesis for supporting vertebral bodies between which a natural disc has been partially or wholly removed comprising:
a) an interbody disc having
an upper ring having an upper surface and a lower ring having a lower surface;
a first annular plate having a first lip extending around a full outer circumference thereof, said first lip being joined to said upper ring around a full circumference thereof, creating an internal slot extending around a full internal circumference of said first lip;
a second annular plate having a second lip extending around a full inner circumference thereof, said second annular plate being joined to said first annular plate around a full inner circumference thereof, creating an external slot extending around a full external circumference of said second lip, the second annular plate being joined to the lower ring;
the rings encompassing one or more continuous or discontinuous internal bone channels of limited cross-sectional area between the upper and lower surfaces to enable bone to form and fuse into one or more continuous or discontinuous struts between the separated vertebral bodies, wherein at least one of said plates has a flexure slot therein, said flexure slot puncturing through said plate from a first plate surface to an opposed plate surface and following a curved path along said plate.

4. The prosthesis of claim 3 wherein the stiffness of the disc is within the range of about 200 to 1500 N/mm.

5. An interbody hybrid spacer comprising:
a support structure formed with upper and lower surfaces adapted to engage the faces of and support adjacent upper and lower vertebrae in a desired spatial relationship while allowing limited movement along and about the longitudinal axis of the supported vertebrae, the support structure having an exterior wall extending between the upper and lower surfaces and one or more centrally disposed generally vertically oriented bone accommodating openings and a plurality of interleaved thin tissue channels for accommodating the infusion of soft tissue therein with certain of the channels extending from a peripheral wall to a location adjacent the central opening(s), but not into the opening(s), the remaining channels extending from and in fluid communication with the central opening(s) to a location adjacent to, but not through, the exterior wall,
wherein the tissue channels are planar and extend generally at a right angle to the longitudinal axis, further including stop means for limiting the compression of the support structure along the longitudinal axis without completely closing the channels to accommodate lateral bending action, wherein the stop means comprises a narrowing of the remaining channels adjacent the central opening(s), and
further including a plate partially obstructing the bone accommodating opening(s) to limit the dimensions of bone material allowed to grow between the supported vertebrae to provide soft fusion.

6. An interbody hybrid spacer for supporting adjacent vertebral bodies between which a natural disc has been partially or fully removed comprising:
a) an upper and lower section;
b) the upper section having a top surface for engaging the face of the upper vertebrae, an outer wall extending continuously from the upper section to the lower section, an inner wall extending continuously from the upper section to the lower section, forming a ring-shaped inner cavity therebetween, the inner wall surrounding an open core the inner and outer walls having a helical slot extending through the inner and outer walls;
c) the lower section being joined to the lower end of the upper section and being formed with an upwardly extending annular post extending into the ring-shaped inner cavity; and
d) the helical slot forming inner and outer springs in the inner and outer walls of the upper section, respectively, wherein the inner spring extends continuously from the upper section to the lower section and the outer spring extends continuously from the upper section to the lower section.

7. The spacer of claim 6 wherein the lower section post is arranged to abut the upper end of the cavity to limit the compression of the upper section without completely closing the helical slot.

8. An interbody hybrid spacer for maintaining adjacent vertebrae in a desired spaced relationship after a natural disc therebetween has been removed comprising:
a) an inner section in the form of a cylinder with a central opening, the cylinder having a spiral slot therein;
b) an outer section having upper and lower portions secured to the exterior wall of the inner section and forming a toroidal opening therein, said toroidal opening extending into an outside of the outer section and encircling the outside of the outer section; and
c) a stop-ring disposed in the toroidal opening with sufficient clearance therein to allow limited flexure and compression of the inner section.

9. An interbody hybrid spacer for supporting adjacent vertebral bodies between which a natural disc has been partially or fully removed comprising:
a) an upper and lower section; b) the upper section, in the form of a cylindrical hub, having an open central core to accommodate bone fusion therein and an outer surface, the hub extending upwardly from a bottom to an outwardly extending flanged head portion terminating in a rim, the flanged head portion having a lower surface;
b) the lower section joined to the bottom of the upper section and having an annular post extending upwardly adjacent the outer surface of the upper section to a location just below the lower surface of the flanged head of the upper section; and c) a spiral slot formed in the cylindrical hub of the upper section for accommodating soft tissue ingrowth and allowing limited articulation of the spacer, the annular post being arranged to engage the lower surface of the flanged head when the spacer is subjected to excessive loads.

10. An intervertebral prosthesis comprising:

an interbody device, said interbody device having an upper surface and an opposed lower surface for engaging faces of adjacent vertebral bodies between which a natural disc has been partially or wholly removed, the interbody device having a wall extending between said upper surface and said lower surface, said wall having a perimeter defining a first wall portion and a second wall portion opposed to said first wall portion, having a central hole through said interbody device, said central hole connecting said upper surface and said lower surface, having at least a first slit originating at said first wall portion and extending inward in a generally horizontal direction stopping before reaching said second wall portion, having at least a second slit originating at said second wall portion and extending inward in a generally horizontal direction stopping before reaching said first wall portion, said first slit and said second slit not intersecting each other, wherein said central hole intersects said first slit and said second slit, wherein said upper surface and said lower surface have a perimeter shape comprising a first end region, a second end region opposed to said first end region, and a middle region located between said first end region and said second end region, wherein said middle region is narrower in a transverse direction than either said first end region or said second end region.

11. The intervertebral prosthesis of claim 10, wherein said central hole, in a cross-section in a plane perpendicular to a longitudinal axis of said central hole, is elongated having a longer dimension and a shorter dimension transverse to said longer dimension.

12. The intervertebral prosthesis of claim 11, wherein said longer dimension of said central hole is at least approximately coincident with a longer dimension of said upper surface of said interbody device.

13. The intervertebral prosthesis of claim 10, wherein said middle region comprises a first indentation on a first side of said upper surface and a second indentation on a second opposed side of said upper surface.

14. The intervertebral prosthesis of claim 10, further comprising a keel protruding from said upper surface or said lower surface of said interbody device.

15. The intervertebral prosthesis of claim 10, wherein said central hole has a cross-sectional area that is about 35% or less of the total area of said upper surface or said lower surface.

16. The intervertebral prosthesis of claim 10, wherein said upper surface or said lower surface has symmetry with respect to at least one plane of symmetry.

* * * * *